United States Patent
San et al.

(10) Patent No.: US 10,774,349 B2
(45) Date of Patent: Sep. 15, 2020

(54) ALPHA OMEGA BIFUNCTIONAL FATTY ACIDS

(71) Applicant: William Marsh Rice University, Houston, TX (US)

(72) Inventors: Ka-Yiu San, Houston, TX (US); Dan Wang, Houston, TX (US)

(73) Assignee: William Marsh Rice University, Houston, TX (US)

( * ) Notice: Subject to any disclaimer, the term of this patent is extended or adjusted under 35 U.S.C. 154(b) by 152 days.

(21) Appl. No.: 15/572,099

(22) PCT Filed: May 7, 2016

(86) PCT No.: PCT/US2016/031386
§ 371 (c)(1),
(2) Date: Nov. 6, 2017

(87) PCT Pub. No.: WO2016/179572
PCT Pub. Date: Nov. 10, 2016

(65) Prior Publication Data
US 2018/0119183 A1      May 3, 2018

Related U.S. Application Data

(60) Provisional application No. 62/158,413, filed on May 7, 2015.

(51) Int. Cl.
| C12P 7/64 | (2006.01) |
| C11B 1/00 | (2006.01) |
| C12N 9/10 | (2006.01) |
| C12N 9/16 | (2006.01) |
| C12N 9/88 | (2006.01) |
| C12N 9/00 | (2006.01) |
| C11C 1/00 | (2006.01) |

(52) U.S. Cl.
CPC .............. *C12P 7/6409* (2013.01); *C11B 1/00* (2013.01); *C11C 1/002* (2013.01); *C12N 9/1029* (2013.01); *C12N 9/13* (2013.01); *C12N 9/16* (2013.01); *C12N 9/88* (2013.01); *C12N 9/93* (2013.01)

(58) Field of Classification Search
None
See application file for complete search history.

(56) References Cited

U.S. PATENT DOCUMENTS 9,994,881 B2 * 6/2018 Gonzalez ............. C12N 9/0006
2016/0090576 A1   3/2016 Garg et al.

FOREIGN PATENT DOCUMENTS

| WO | WO2000075343 | 12/2000 |
| WO | WO2016179572 | 11/2016 |

OTHER PUBLICATIONS

Choi, K. H., R. J. Heath, and C. O. Rock. 2000. β-Ketoacyl-acyl carrier protein synthase III (FabH) is a determining factor in branched-chain fatty acid biosynthesis. J. Bacteriol. 182:365-370.
He, X., and K. A. Reynolds. 2002. Purification, characterization, and identification of novel inhibitors of the beta-ketoacyl-acyl carrier protein synthase III (FabH) from *Staphylococcus aureus*. Antimicrob. Agents Chemother. 46:1310-1318.
Qiu, X, et al., Crystal structure and substrate specificity of the b-ketoacyl-acyl carrier protein synthase III (FabH) from *Staphylococcus aureus*, Protein Science (2005), 14:2087-2094 (2005).
Wu et al. "Efficient odd straight medium chain free fatty acid production by metabolically engineered *Escherichia col i*," Biotechnol Bioeng. Jul. 14, 2014 (Jul. 14, 2014), vol. 111, pp. 2209-2219.
Traavik et al. "Chapter 4:Genetic Engineering of Living Cells and Organisms," Biosafety First, Ed.Traavik, 2007, pp. 1-23.

\* cited by examiner

*Primary Examiner* — Suzanne M Noakes
*Assistant Examiner* — Jae W Lee
(74) *Attorney, Agent, or Firm* — Boulware & Valoir

(57) ABSTRACT

The present disclosure describes an engineered microorganism for producing alpha omega bifunctional C6-16 fatty acids from renewable carbon sources.

15 Claims, 4 Drawing Sheets

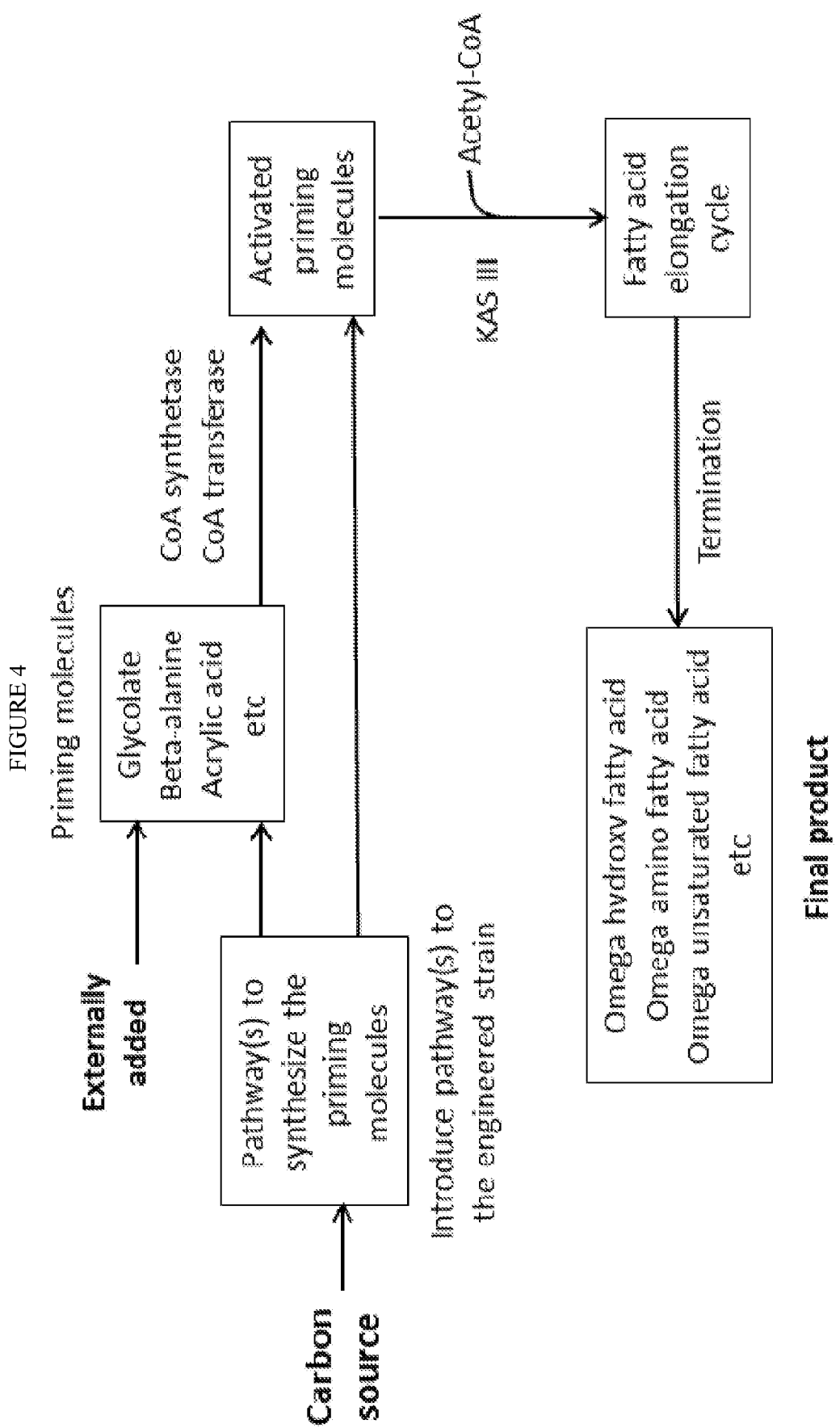

ALPHA OMEGA BIFUNCTIONAL FATTY ACIDS

PRIOR RELATED APPLICATIONS

This application is a National Phase under 35 U.S.C. § 371 of International Application PCT/US16/31386, filed May 7, 2016, which claims priority to U.S. Ser. No. 62/158,413 filed May 7, 2015. Both applications are expressly incorporated by reference herein in their entirety for all purposes.

FEDERALLY SPONSORED RESEARCH STATEMENT

This invention was made with government support under Grant No: EEC-0813570 awarded by the NSF. The government has certain rights in the invention.

FIELD OF THE DISCLOSURE

This invention relates generally to a microbial method to synthesize bifunctional short- to medium-carbon chain length fatty acids, in particular, alpha-omega bifunctional fatty acids, such as, omega hydroxyl fatty acids.

BACKGROUND OF THE DISCLOSURE

Hydroxy fatty acids are widely used for making polymers and are also valuable in chemical, cosmetic and food industries as starting materials for synthesis of lubricants, adhesives, and cosmetic ingredients. Similarly, dicarboxylic fatty acids have many industrial applications, such as synthesis of copolymers like polyamides and polyesters, coatings, adhesives, greases, polyesters, dyestuffs, detergents, flame retardants, cosmetic ingredients, and fragrances. For example, adipic acid (n=6) is among the top 50 bulk manufactured chemicals in US, and primarily used for manufacturing nylon. Sebacic acid (n=8) and its derivatives have many applications and are used in manufacturing plasticizers, lubricants, and cosmetics. Dodecanedioic acid (n=12) is used in the production of nylon (nylon-6,12) and polyamides.

Hydroxy fatty acids and dicarboxylic fatty acids are typically produced by a chemical process, or microbial transformation of aliphatic hydrocarbons and fatty acids. However, it would be of benefit to make these valuable chemicals starting with common, renewable carbon sources, such as glucose, glycerol, and the like.

SUMMARY OF THE DISCLOSURE

The biochemical mechanism of fatty acid biosynthesis is universally similar among all organisms. Generally, fatty acids are synthesized by the repeated iteration of four-reactions, which start with an acyl-COA primer, which is elongated, two carbons per cycle, using carbon atoms derived from a malonyl moiety. The four sequential reactions that make up this cycle generate 3-ketoacyl-thioester, 3-hydroxyacyl-thioester, and 2-enoyl-thioester derivative intermediates, and finally an acyl-thioester derivative that is two carbons longer than the initial acyl-CoA primer.

In bacteria, typified by the *E. coli* system and higher plant plastids, these reactions are catalyzed by a dissociable, type II fatty acid synthase that is composed of the four enzymes 3-ketoacyl-ACP synthase (KAS), 3-ketoacyl-ACP reductase (encoded by fabG), 3-hydroxyacyl-ACP dehydratase (encoded by fabA), and enoyl-ACP reductase (encoded by fabI).

In the type II fatty acid synthase system, there are three genetically and biochemically distinct KAS isomers, namely KASI (encoded by fabB), KASII (encoded by fabF), and KASIII (encoded by fabH). Their functions have been studied extensively in *E. coli*. They differ in their specificities for acyl-thioester substrates, having optimum activities for substrates of different acyl-chain lengths and different thioesters. While KASI and KASII catalyze the condensation between acyl-ACP (of longer acyl-chain length) with malonyl-ACP substrates, KASIII specifically utilizes acetyl-CoA as a substrate for the condensing reaction with malonyl-ACP, and thus initiates fatty acid biosynthesis.

In this disclosure, summarized in FIG. 4, we demonstrate the production of omega functionalized fatty acids by engineering bacteria to have an overexpressed KASIII enzyme with substrate specificity such that it can convert:

$$R\text{—}CH_{2(0-n)}CO\text{—}CoA + \text{malonyl-[ACP]} + H^+$$
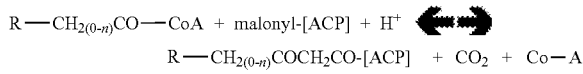
$$R\text{—}CH_{2(0-n)}COCH_2CO\text{-[ACP]} + CO_2 + Co\text{—}A$$

wherein R is a functional group, including a hydroxy, amine, branch, carboxyl, double bond, a benzoyl group, a cyclic group, a halogen group, and the like. n=0 to 10, and can be changed by chaining the TE.

The remaining FAS enzymes are used to grow the omega functionalized fatty acid, and a TE with the desired length preference is also overexpressed and can free the resulting omega-functionalized fatty acid. Preferably, the microbe is also engineered to make the desired $R\text{—}CH_{2(0-n)}CO\text{-CoA}$ starting material. In this way, the can be grown on standard carbon sources, such as glycerol, glucose, sucrose, fructose, inositol, arabitol, xylose, cellulose, saccharose, as well as on waste resources such as corn steep liquor, and the like. If desired, the resulting omega functionalized fatty acid can be further converted to other desirable products.

By "omega", herein, we refer to the end of the growing straight chain fatty acid opposite the ACP. The nomeculature remains even after cleavage from the ACP. Thus, the last carbon in the growing straight chain is the omega position. In this molecule, for example, the hydroxyl is on the omega carbon, while the alpha carbon is the carboxylate:

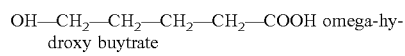
OH—$CH_2$—$CH_2$—$CH_2$—$CH_2$—COOH omega-hydroxy buytrate

Two separate approaches have been demonstrated using the production of omega hydroxy fatty acid as examples.

In the first approach, omega hydroxy fatty acid (specifically 16-hydroxyhexanoic acid) was produced by the metabolically engineered strain by adding glycolate for use as a recursor to the initiating primer for fatty acid synthesis and using an acyl-ACP thioesterase (TE) from *Ricinus communis*.

In second approach, the strains were further engineered to produce glycolate in vivo from a renewable carbon source, such as glucose. These further engineered strains thus are capable of producing e.g., 16-hydroxyhexanoic acid directly from glucose.

In yet another example, 14-hydroxymyristic acid was produced by using a TE from *Umbellularia californica*.

The method makes use of the following design features:
1. Special β-ketoacyl-acyl carrier protein synthase III (KASIII) are overexpressed and used to initiate the fatty acid synthesis cycle by incorporating an omega functionalized intiator primer. The primer is omega functionalized, rather than being the usual acetyl-CoA or prionyl-coA. Further, the intiator primer can be longer than 2 or 3 carbons, as KASII enzymes are available with longer chain substrate specificity.
2. The promiscuous nature of the fatty acid elongation cycle allows extension of the carbon chain length (by 2 carbons) with omega-functional groups.
3. The promiscuous nature of the acyl-ACP thioesterase or "TE" allows release of free alpha-omega fatty acid from acyl-ACP.
4. In addition, the priming precursor is activated by a selected CoA synthase, if needed. Some CoA synthases have broader specificity and may suffice for some primers. For others, a specific CoA synthase with the requisite activity will need to be added to the cell.
5. In addition, in preferred embodiments, we also introduce an engineered pathway(s) to synthesize the omega-functionalized priming molecule from renewable sources, such as glucose, glycerol, and the like.
6. Chain length is modulated by adding an overexpressed TE of the requisite specificity.

This is the first demonstration of engineered *E. coli* strain to produce ω-hydroxy fatty acid from glucose without any exogenous fatty acid addition and heterogenous hydroxyl enzyme overexpression.

The novel genetically engineered strains provide an alternative method for production of hydroxy fatty acids and dicarboxylic fatty acids and the like using microbial fermentation. The advantages of using these genetically engineered strains are as follows:
1. Ability to produce alpha-omega bifunctional fatty acids, such as hydroxy fatty acids and dicarboxylic fatty acids, of different chain length using different strain designs customized to produce specific chain length free fatty acids.
2. Extension of fatty acid synthesis pathway to produce new fatty acid derivatives that do not accumulate in the wild type microbe.
3. Ability to produce high value-added products using a non-destructive and environmentally friendly methods.
4. Utilization of inexpensive raw renewable feedstock as fermentation materials. Some of the genes discussed herein include those in the following table.

| Strain | Gene | Accession no or Gene ID | Protein_ID |
|---|---|---|---|
| *Cuphea hookeriana* | fatB2 | U39834.1 | AAC49269 |
| *Ricinus communis* | fatA | EF495065.1 | ABS30422.1 |
| *Umbellularia californica* | fatB | Q41635.1 | Q41635 |
| *Arabidopsis thaliana* | GLYR | AY044183 (EC: 1.1.1.2) | Q9LSV0 |
| *Escherichia coli* | aceA | b4015, ECK4007 (EC: 4.1.3.1) | P0A9G6 |
| *Pseudomonas putida* P1 | alkJ | AJ233397 (EC: 1.1.99.-) | CAB51051.1 |
| *Pseudomonas putida* P1 | alkH | AJ233397 (EC: 1.1.99.-) | CAB51050.1 |
| *Staphlococcus aureus* | fabH | Kegg SACOL0987 | Q8NXE2 |
| *Streptomyces glaucescens* | fabH | L43074.1 (EC: 2.3.1.180) | Q54206 |

The methods described herein allow the efficient production of alpha-omega bifunctional fatty acids of various carbon chain lengths from renewable sources. The alpha-omega bifunctional fatty acids include: omega hydroxyl fatty acid, alpha-omega dicarboxylic acid, omega amino fatty, and omega unsaturated fatty acids.

As used herein, a "primer" is a starting molecule for the FAS cycle to add two carbon donor units to. The "initiating primer" or "initiator primer" is normally acetyl-ACP or propionyl-ACP, but as the chain grows by adding donor units in each cycle, the "primer" will accordingly increase in size by two carbons (as well as be in ACP form, rather than coA form). In this case, the bacteria uses non-traditional primers to make the atypical alpha omega fatty acids products described herein.

As used herein, a "primer precursor" is a starting molecule activating by conversion to its acyl-coA form, which then functions as the initiating primer. Subsequent primers are longer in each cycle by 2 carbons and are attached to ACP, as the coA is lost in the first condensation.

Suitable primer precursors include glycolate (which produces w-hydroxy fatty acids), beta alanine (produces ω-amino fatty acids), and the primer propenoyl-CoA (for making ω-unsaturated fatty acids). Examples of primer precursors leading to the final bi-functional fatty acids are listed below:

| Priming molecules | Enzymes requiring in the production | Final products |
|---|---|---|
| Glycolate | PrpE (a propionyl-CoA synthetase)<br>FabH (a β-ketoacyl-ACP synthase III)<br>TE (acyl-ACP thioesterase) or similar enzymes | ω-hydroxy fatty acids |
| Beta alanine | PrpE (a propionyl-CoA synthetase)<br>FabH (a β-ketoacyl-ACP synthase III)<br>TE (acyl-ACP thioesterase) or similar enzymes | ω-amino fatty acids |
| Acrylic acid | PrpE (a propionyl-CoA synthetase)<br>FabH (a β-ketoacyl-ACP synthase III)<br>TE (acyl-ACP thioesterase) or similar enzymes | ω-unsaturated fatty acids |

The experiments to confirm FabH activity with beta alanine and acylic acid as substrates are not yet complete, but given the known activity of KASIII for a large number of substrates, it is expected to be functional with these substrates as well (Qiu 2005).

As used herein, the "donor" of the 2 carbon units is malonyl-CoA. It might also be called an "extender."

As used herein "type II fatty acid synthesis enzymes" refer to those enzymes that function independently, e.g., are discrete, monofunctional enzymes, used in fatty acid synthesis. Type II enzymes are found in archaea and bacteria. Type I systems, in contrast, utilize a single large, multifunctional polypeptide.

As used herein, KASIII is an enzyme, usually from bacteria or plant chloroplasts, that functions as a ketoacyl-ACP synthase (13 acyl-acyl carrier protein synthase or acetoacetyl-ACP synthase; EC Number: 2.3.1.180) that catalyzes the reaction:

acyl-CoA+a malonyl-[ACP]+H$^+$<=> an acetoacyl-[ACP]+CO$_2$+Co-A

Of course, an enzyme with broad substrate specificity should be used, so that one is not limited in the choice of initiating primers. In many Gram-positive bacteria (i.e., *Bacillus subtilis, Streptomyces glaucescens,* and *Staphylococcus aureus*), KASIII can utilize both branched-chain and straight-chain substrates, resulting in the production of both branched- and straight-chain fatty acids. For example, two *B. subtilis* KASIII-encoding genes, bfabHA (yjaX) and bfabHB (yhfB), have been characterized, and these have the capacity to catalyze the condensation of branched acyl-CoAs with malonyl-ACP. In contrast, KASIII from Gram-negative bacteria (e.g., *E. coli*) appear to prefer straight-chain acyl-CoA substrates, which results in the production of straight-chain fatty acids. Thus, the KASIII from Gram-positive microbes may be preferred.

Examples of suitable KASIII enzymes include a β-ketoacyl-ACP synthase III from *Staphylococcus aureus*. The rank order of activity of *S. aureus* FabH with various acyl-CoA primers was as follows: isobutyryl→hexanoyl→butyryl→isovaleryl→> acetyl-CoA. *S. pneumoniae* FabH has similar substrate specificity, (a Gram positive bacteria) is able to utilize both straight- and branched-chain (C4-C6) acyl CoA primers.

The *Streptomyces glaucescens* KASIII (fabH gene) also has unusually broad specificity for acyl-CoA substrates, with Km values of 2.4 μM for acetyl-CoA, 0.71 μM for butyryl-CoA, and 0.41 μM for isobutyryl-CoA.

The KASIII from family KS1 (ketoacyl synthase 1) from www.enzyme.cbirc.iastate.edu (incorporated herein by reference for its teachings regarding KASIII) is also suitable, as is KASIII from *A. acidocaldarius, B. vulgatus* KASIII, and KASIII from *Legionella pneumophila, Aeromonas hydrophila, Bacteroides vulgatus, Brevibacterium linens, Capnocytophaga gingivalis, Thermus aquaticus, Bacillus licheniformis, Desulfovibrio vulgaris, Bacillus subtilis* subsp. *S. Haliangium ochraceum, Alicyclobacillus acidocaldarius,* and the like. A partial listing of available KASIII enzymes is provided in FIG. 5. Further, WO2000075343 describes method of engineering KAS enzymes to change their substrate specificity.

As used herein, a "coA synthase than can activate a primer precursor to an omega-functionalized primer" is an enzyme with broad enough substrate specificity to convert:

R—CH$_{2(0-n)}$CO+CoA←→R—CH$_{2(0-n)}$COCH$_2$CO-CoA

Generally speaking, such enzymes are encoded by prpE (EC:6.2.1.17) and enzymes with broad specificity can be dound in the same organisms as those having KASII with broad specificity. See e.g., P55912. Other proteins that can be used include "PCT" or Propionate-CoA transferase (EC 2.8.3.1); 3-hydroxypropionyl-CoA synthase (EC 6.2.1.36); and Propionate-CoA ligase (EC 6.2.1.17).

As used herein a "3-oxoacyl-[acyl-carrier-protein]reductase" or "3-oxoacyl-[ACP]reductase" is an enzyme that catalyzes the reduction of a ß-ketoacyl-ACP to a (3R)-ß-hydroxyacyl-ACP:

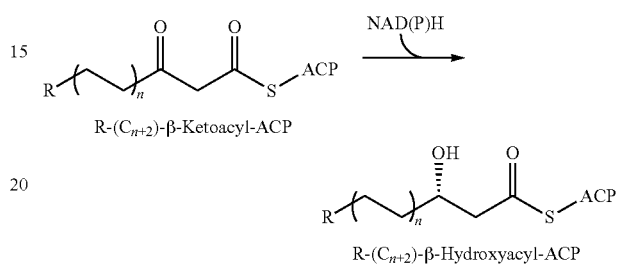

R-(C$_{n+2}$)-β-Ketoacyl-ACP

R-(C$_{n+2}$)-β-Hydroxyacyl-ACP

As used herein, a "3-hydroxyacyl-[ACP] dehydratase" is an enzyme that catalyzes the dehydration of a (3R)-ß-hydroxyacyl-ACP to a transenoyl-ACP:

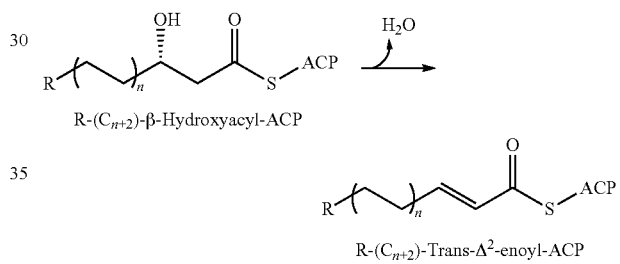

R-(C$_{n+2}$)-β-Hydroxyacyl-ACP

R-(C$_{n+2}$)-Trans-Δ$^2$-enoyl-ACP

As used herein, an "enoyl-[ACP]reductase" that catalyzes the reduction of a transenoyl-ACP to an acyl-ACP:

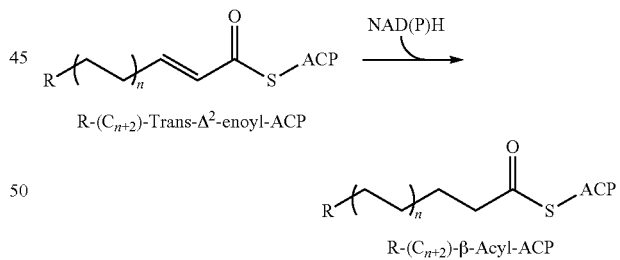

R-(C$_{n+2}$)-Trans-Δ$^2$-enoyl-ACP

R-(C$_{n+2}$)-β-Acyl-ACP

Many examples of FAS enzymes catalyzing these reactions are provided herein and the following table provides a few examples:

TABLE A

Example FAS Enzymes for Cycle Reaction Steps (See above for reaction illustrations)

| Reaction | Source organism and gene name | Protein Accession Numbers |
|---|---|---|
| β-ketoacyl-ACP → (3R)-β-hydroxyacyl-ACP | *E. coli* fabG | NP_415611.1 |

TABLE A-continued

Example FAS Enzymes for Cycle Reaction
Steps (See above for reaction illustrations)

| Reaction | Source organism and gene name | Protein Accession Numbers |
|---|---|---|
| (3R)-β-hydroxyacyl-ACP → transenoyl-ACP | E. coli fabA | NP_415474.1 |
| | E. coli fabZ | NP_414722.1 |
| transenoyl-ACP → acyl-ACP | E. coli fabI | NP_415804.1 |
| | Enterococcus faecalis fabK | NP_816503.1 |
| | Bacillus subtilis fabL | KFK80655.1 |
| | Vibrio cholerae fabV | ABX38717.1 |

As used herein "termination pathway" refers to one or more enzymes (or genes encoding same) that will pull reaction intermediates out the FAS cycle and produce the desired end product. The most common termination enzyme is an overexpressed acyl-ACP thioesterase. Many microbes do not make significant amounts of free fatty acids, but can be made to do so by adding a gene coding for an acyl-ACP thioesterase (called a "TE" gene herein).

Acyl-acyl carrier protein (ACP) thioesterase or TE is an enzyme that terminates the intraplastidial fatty acid synthesis by hydrolyzing the acyl-ACP intermediates and releasing free fatty acids. These enzymes are classified in two families, FatA and FatB, which differ in amino acid sequence and substrate specificity. Generally speaking, the N terminal (aa 1-98) of any acyl-ACP thioesterase controls the substrate specificity of the enzyme, and it is known how to change substrate specificity by swapping amino terminal domains.

Many acyl-ACP thioesterase proteins are known and can be added to microbes for use as termination enzymes (e.g., CAA52070, YP_003274948, ACY23055, AAB71729, BAB33929, to name a few of the thousands of such proteins available). Such genes can be added by plasmid or other vector, or can be cloned directly into the genome. In certain species, it may also be possible to genetically engineer the endogenous protein to be overexpressed by changing the regulatory sequences or removing repressors. However, overexpressing the gene by inclusion on selectable plasmids that exist in hundreds of copies in the cell may be preferred due to its simplicity, although permanent modifications to the genome may be preferred in the long term for stability reasons.

Other fatty acyl ACP thioesterases include Umbellularia californica (GenBank AAC49001, Q41635), Cinnamomum camphora (Q39473), Myristica fragrans (AAB71729, AAB71730), Elaeis guineensis (ABD83939, AAD42220, AAL15645), Populus tomentosa (ABC47311), Arabidopsis thaliana (NP_172327, CAA85387, CAA85388), Gossypium hirsutum (Q9SQI3, AAD01982), Cuphea lanceolata (CAA54060, CAC19933), Cuphea hookeriana (AAC72882, AAC49269, AAC49269, Q39513), Cuphea calophylla subsp. mesostemon (ABB71581), Vitis vinifera (CAN81819), Garcinia mangostana (AAB51525), Brassica juncea (ABI118986), Madhuca longifolia (AAX51637), Brassica napus (ABH11710), and Oryza sativa (EAY86877, EAY99617, NP-001068400). Other TEs include the TesA or TesB from E. coli or YJR019C, YTE1 or YTE2 from yeast or the TE from humans or other mammals.

In some embodiments, at least one TE gene is from a plant, for example overexpressed acyl-ACP thioesterase gene from Ricinus communis, Jatropha curcas, Diploknema butyracea, Cuphea palustris, or Gossypium hirsutum, or an overexpressed hybrid acyl-ACP thioesterase comprising different thioesterase domains operably fused together (see WO2011116279, incorporated by reference herein in its entirety for all purposes). Preferably, the hybrid thioesterase includes a terminal region of the acyl-ACP thioesterase from Ricinus communis or a 70, 80, 90 or 95% homolog there to operably coupled to the remaining portion of the thioesterase from another species. In such manner, enzyme specificity can be tailored for the use in question.

In particular, the microorganism can comprise an overexpressed hybrid acyl-ACP thioesterase comprising the amino terminal region of the thioesterase from Ricinus communis operably coupled to the carboxyl region of the thioesterase from another species. Such microorganisms can be combined with each of the other mutations and overexpressions described herein in any combination.

It is also known to change the chain length of the FFAs by changing the TE. Class I acyl-ACP TEs act primarily on 14- and 16-carbon acyl-ACP substrates; 2) Class II acyl-ACP TEs have broad substrate specificities, with major activities toward 8- and 14-carbon acyl-ACP substrates; and 3) Class III acyl-ACP TEs act predominantly on 8-carbon acyl-ACPs.

For example, most thioesterases exhibit the highest specificities in the C16-C18 range, including A. thaliana FatA (18:1Δ9), Madhuca longifolia FatB (16:0, 16:1, 18:0, 18:1), Coriandrum sativum FatA (18:1Δ9), A. thaliana FatB (16:0, 18:1, 18:0, 16:1), Helianthus annuus FatA (18:1, 16:1), and Brassica juncea FatB2 (16:0, 18:0), among numerous others. Medium-chain acyl-ACP thioesterases include Cuphea palustris FatB1 and C. hookeriana FatB2 (8:0, 10:0), C. palustris FatB2 (14:0, 16:0); and Umbellularia californica FatB (12:0, 12:1, 14:0, 14:1). Arecaceae (palm family) and Cuphea accumulate large quantities of fatty acids that are shorter (between 8 and 12 carbon atoms), and several enzymes are also available in bacteria. Exemplary thioesterase families and common names of their members are shown in Table B:

TABLE B

Thioesterase Families and Common Names of their Members

| Family | Producing organisms | Genes and/or other names of family members |
|---|---|---|
| TE1 | A, B, Ea | Ach1 |
| TE2 | A, B, E | Acot1-Acot6, BAAT thioesterase |
| TE3 | A, B | tesA, acyl-CoA thioesterase I, protease I, lysophospholipase L1 |
| TE4 | B, E | tesB, acyl-CoA thioesterase II, Acot8 |
| TE5 | B | tesC (ybaW), acyl-CoA thioesterase III |
| TE6 | A, B, E | Acot7 (BACH), Acot11 (BFIT, Them1), Acot12 (CACH), YciA |
| TE7 | B, E | Acot9, Acot10 |
| TE8 | A, B, E | Acot13 (Them2) |
| TE9 | B | YbgC |

TABLE B-continued

Thioesterase Families and Common Names of their Members

| Family | Producing organisms | Genes and/or other names of family members |
|---|---|---|
| TE10 | B | 4HBT-I |
| TE11 | B | 4HBT-II, EntH (YbdB) |
| TE12 | B,E | DNHA-CoA hydrolase |
| TE13 | A, B | paaI, paaD |
| TE14 | B,E | FatA, FatB |
| TE15 | B | Thioesterase CalE7 |
| TE16 | A, B, E | TE domain of FAS (Thioesterase I), TE domain of PKS or NRP (type I thioesterase (TE I)) |
| TE17 | B | TE domain of PKS |
| TE18 | B,E | Thioesterase II, type II thioesterase (TE II) |
| TE19 | B | luxD |
| TE20 | E | ppt1, ppt2, palmitoyl-protein thioesterase |
| TE21 | A, B, E | apt1, apt2, acyl-protein thioesterase, phospholipase, carboxylesterase |
| TE22 | A, B, E | S-formylglutathione hydrolase, esterase A, esterase D |
| TE23 | A, B, E | Hydroxyglutathione hydrolase, glyoxalase II | aA, archaea;
B, bacteria;
E, eukaryota.
Most prevalent producers bolded

TE is not the only termination enzyme, and multiple enzymes can be used to provide a variety of final products. Many examples of termination pathways are provided herein and the following Table C provides several examples:

TABLE C

Termination Pathways for Conversion of ACP Intermediates to Desired Products

| Reaction | Illustration | EC Numbers | Enzyme names | Source organism and gene name | Protein Accession Numbers |
|---|---|---|---|---|---|
| Acyl-ACP→ Carboxylic acid | Acyl-ACP → Carboxylic Acid | 3.1.2.- | Thioesterase | E. coli tesA | NP 415027.1 |
| | | | | Cuphea palustris fatB1 | AAC49179.1 |
| | | | | Cuphea viscosissima fatB3 | AEM72524.1 |
| | | | | Ulmus americana fatB1 | AAB71731.1 |
| | | | | Cocos nucifera fatB2 | AEM72520.1 |
| | | | | Elaeis guineensis PTE | AAD42220.2 |
| | | | | Clostridium perfringens CPF 2954 | ABG82470.1 |
| | | | | Umbellularia californica fatB1 | AAA34215.1 |
| Acyl-ACP→ Alcohol | Acyl-ACP → Primary Alcohol | 1.2.1.- | Alcohol-forming ACP reductase | Marinobacter aquaeolei VT8 maqu_2220 | YP_959486.1 |
| | | | | Hahella chejuensis hch_05075 | ABC31758.1 |
| | | | | Marinobacter algicola MDG893_11561 | A6EVI7 |
| | | | | Bermanella marisrubri RED65_09894 | Q1N697 |
| Acyl-ACP→ Aldehyde | Acyl-ACP → Aldehyde | 1.2.1.80 | Aldehyde forming ACP reductase | Nostoc punctiforme Npun_R1710 | ACC80381.1 |
| | | | | Synechococcus elongates Synpcc7942_1594 | Q54765 |
| | | | | Prochlorococcus marinus P9515_05971 | A2BVJ5 |
| | | | | Synechocystis sp. PCC 6803 sll0209 | YP_005652204.1 |

TABLE C-continued

Termination Pathways for Conversion of ACP Intermediates to Desired Products

| Reaction | Illustration | EC Numbers | Enzyme names | Source organism and gene name | Protein Accession Numbers |
|---|---|---|---|---|---|
| Aldehyde→ Alcohol | An aldehyde → An alcohol | 1.1.1.- | Alcohol dehydrogenase | E. coli betA<br>E. coli dkgA<br>E. coli eutG<br>E. coli fucO<br>E. coli ucpA<br>E. coli yahK<br>E. coli ybbO<br>E. coli ybdH<br>E. coli yiaY<br>E. coli yjgB | NP_414845.1<br>NP_417485.4<br>NP_416948.4<br>NP_417279.2<br>NP_416921.4<br>NP_414859.1<br>NP_415026.1<br>NP_415132.1<br>YP_026233.1<br>NP_418690.4 |
| Aldehyde→ Alkane | An aldehyde → An alkane | 4.1.99.5 | Aldehyde decarbonylase | Synechococcus elongatus PCC7942 orf1593<br>Nostoc punctiforme PCC73102 npun_R1711<br>Prochlorococcus marinus MIT9313 pmt1231 | Q54764.1<br><br>B2J1M1.1<br><br>Q7V6D4.1 |
| Aldehyde→ Amine | An aldehyde → An amine | 2.6.1.- | Transaminase | Arabidopsis thaliana At3g22200<br>Alcaligenes denitrificans AptA<br>Bordetella bronchiseptica BB0869<br>Bordetella parapertussis BPP0784<br>Brucella melitensis BAWG_0478<br>Burkholderia pseudomallei BP1026B_I0669<br>Chromobacterium violaceum CV2025<br>Oceanicola granulosus OG2516_07293<br>Paracoccus denitrificans PD1222 Pden_3984<br>Pseudogulbenkiania ferrooxidans ω-TA<br>Pseudomonas putida ω-TA<br>Ralstonia solanacearum ω-TA<br>Rhizobium meliloti SMc01534<br>Vibrio fluvialis ω-TA<br>Mus musculus abaT<br>E. coli gabT | NP_01189947.1<br><br>AAP92672.1<br><br>WP_015041039.1<br><br>WP_010927683.1<br><br>EEW88370.1<br><br>AFI65333.1<br><br>AAQ59697.1<br><br>WP_007254984.1<br><br>ABL72050.1<br><br>WP_008952788.1<br><br>P28269.1<br><br>YP_002258353.1<br><br>NP_386510.1<br><br>AEA39183.1<br>AAH58521.1<br>YP_490877.1 |
| Carboxylic Acid→ ω-hydroxy-acid | Carboxylic Acid → ω-Hydroxy-Carboxylic Acid | 1.14.- | Carboxylic acid omega hydroxylase | Pseudomonas putida alkBGT<br>Marinobacter aquaeolei CYP153A<br>Mycobacterium marinum CYP153A16<br>Polaromonas sp. CYP153A<br>Nicotiana tabacum CYP94A5<br>Vicia sativa CYP94A1<br>Vicia sativa CYP94A2<br>Arabidopsis thaliana CYP94B1 | YP_009076004.1, Q9WWW4.1, Q9L4M8.1<br>ABM17701.1<br><br>YP_001851443.1<br><br>YP_548418.1<br><br>AAL54887.1<br><br>AAD10204.1<br>AAG33645.1<br>BAB08810.1 |

TABLE C-continued

Termination Pathways for Conversion of ACP Intermediates to Desired Products

| Reaction | Illustration | EC Numbers | Enzyme names | Source organism and gene name | Protein Accession Numbers |
|---|---|---|---|---|---|
| | | | | Arabidopsis thaliana CYP86A8 | CAC67445.1 |
| | | | | Candida tropicalis CYP52A1 | AAA63568.1, AAA34354.1, AAA34334.1 |
| | | | | Candida tropicalis CYP52A2 | AAA34353.2, CAA35593.1 |
| | | | | Homo sapiens CYP4A11 | AAQ56847.1 |
| ω-hydroxy-acid→ ω-oxo-acid | ω-Hydroxy-Carboxylic Acid → ω-Oxo-Carboxylic Acid | 1.1.1- | Alcohol oxidase/ alcohol dehydro- genase | Rhodococcus ruber SC1 cddC | AAL14237.1 |
| | | | | Acinetobacter sp. SE19 chnD | AAG10028.1 |
| | | | | E. coli yahK | NP_414859.1 |
| | | | | E. coli yjgB | NP_418690.4 |
| ω-oxo-acid→ dicarboxylic acid | ω-Oxo-Carboxylic Acid → Dicarboxylic Acid | 1.2.1- | Aldehyde dehydro- genase | Rhodococcus ruber SC1 cddD | AAL14238.1 |
| | | | | Acinetobacter sp. SE19 chnE | AAG10022.1 |
| Carboxylic Acid→ α-hydroxy-acid | A carboxylic acid → An alpha-hydroxy-carboxylic acid | 1.14.- | Carboxylic acid alpha hydroxylase | Myxococcus xanthus MXAN_0191 | YP_628473.1 |
| | | | | Stigmatella aurantiaca STIAU_3334 | YP_003957653.1 |

Initial cloning experiments have proceeded in *E. coli* for convenience since most of the required genes are already available in plasmids suitable for bacterial expression, but the addition of genes to bacteria is of nearly universal applicability. Indeed, since recombinant methods were invented in the 70's and are now so commonplace, even school children perform genetic engineering experiments using bacteria. Such species include e.g., *Bacillus, Streptomyces, Azotobacter, Trichoderma, Rhizobium, Pseudomonas, Micrococcus, Nitrobacter, Proteus, Lactobacillus, Pediococcus, Lactococcus, Salmonella, Streptococcus, Paracoccus, Methanosarcina*, and *Methylococcus*, or any of the completely sequenced bacterial species. Indeed, hundreds of bacterial genomes have been completely sequenced, and this information greatly simplifies both the generation of vectors encoding the needed genes, as well as the planning of a recombinant engineering protocol. Such species are listed along with links at en.wikipedia.org/wiki/List_of_sequenced_bacterial_genomes.

Additionally, yeasts, such as *Saccharomyces*, are a common species used for microbial manufacturing, and many species can be successfully transformed. Indeed, yeast are already available that express recombinant thioesterases—one of the termination enzymes described herein—and the reverse beta oxidation pathway has also been achieved in yeast. Other species include but are not limited to *Candida, Aspergillus, Arxula adeninivorans, Candida boidinii, Hansenula polymorpha (Pichia angusta), Kluyveromyces lactis, Pichia pastoris*, and *Yarrowia lipolytica*, to name a few.

It is also possible to genetically modify many species of algae, including e.g., *Spirulina, Apergillus, Chlamydomonas, Laminaria japonica, Undaria pinnatifida, Porphyra*,

*Eucheuma, Kappaphycus, Gracilaria, Monostroma, Enteromorpha, Arthrospira, Chlorella, Dunaliella, Aphanizomenon, Isochrysis, Pavlova, Phaeodactylum, Ulkenia*, Haematococcus, *Chaetoceros, Nannochloropsis, Skeletonema, Thalassiosira*, and *Laminaria japonica*, and the like. Indeed, the microalga *Pavlova lutheri* is already being used as a source of economically valuable docosahexaenoic (DHA) and eicosapentaenoic acids (EPA), and *Crypthecodinium cohnii* is the heterotrophic algal species that is currently used to produce the DHA used in many infant formulas.

Furthermore, a number of databases include vector information and/or a repository of vectors and can be used to choose vectors suitable for the chosen host species. See e.g., AddGene.org, which provides both a repository and a searchable database allowing vectors to be easily located and obtained from colleagues. See also Plasmid Information Database (PlasmID) and DNASU having over 191,000 plasmids. A collection of cloning vectors of *E. coli* is also kept at the National Institute of Genetics as a resource for the biological research community. Furthermore, vectors (including particular ORFS therein) are usually available from colleagues.

The enzymes can be added to the genome or via expression vectors, as desired. Preferably, multiple enzymes are expressed in one vector or multiple enzymes can be combined into one operon by adding the needed signals between coding regions. Further improvements can be had by overexpressing one or more, or even all of the enzymes, e.g., by adding extra copies to the cell via plasmid or other vector. Initial experiments may employ expression plasmids hosting 3 or more ORFs for convenience, but it may be preferred to insert operons or individual genes into the genome for long term stability.

Still further improvements in yield can be had by reducing competing pathways, such as those pathways for making e.g., acetate, formate, ethanol, and lactate, and it is already well known in the art how to reduce or knockout these pathways. See e.g., the Rice patent portfolio by Ka-Yiu San and George Bennett (U.S. Pat. Nos. 7,569,3807,262,046, 8,962,272, 8,795,991) and patents by these inventors (U.S. Pat. Nos. 8,129,157 and 8,691,552) (each incorporated by reference herein in its entirety for all purposes). Many others have worked in this area as well.

Reactions and the enzymes that catalyze said reactions described herein are understood to operate both in the direction described or illustrated, as well as in the reverse direction unless otherwise stated or known to be irreversible. Further, reference to an acid includes the base form, unless it is clear from the context. Thus, reference to succinic acid includes succinate and vice versa.

As used herein, the expressions "microorganism," "microbe," "strain" and the like may be used interchangeably and all such designations include their progeny. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, reference to a "cell," "microbe," "bacteria" etc. is generally understood to include a culture of such cells, as the work described herein is done in cultures having $10^{8-15}$ cells/ml.

As used herein, "growing" cells used in its art accepted manner, referring to exponential growth of a culture of cells, not the few cells that may not have completed their cell cycle at stationary phase or have not yet died in the death phase or after harvesting.

As used in the claims, "homolog" means an enzyme with at least 40% identity to one of the listed sequences and also having the same general catalytic activity, although of course Km, Kcat, and the like can vary. While higher identity (60%, 70%, 80%) and the like may be preferred, it is typical for bacterial sequences to diverge significantly (40-60%), yet still be identifiable as homologs, while mammalian species tend to diverge less (80-90%).

Reference to proteins herein can be understood to include reference to the gene encoding such protein. Thus, a claimed "permease" protein can include the related gene encoding that permease. However, it is preferred herein to refer to the protein by standard name per ecoliwiki or HUGO since both enzymatic and gene names have varied widely, especially in the prokaryotic arts.

Once an exemplary protein is obtained, many additional examples proteins of similar activity can be identified by BLAST search. Further, every protein record is linked to a gene record, making it easy to design expression vectors. Many of the needed enzymes are already available in vectors, and can often be obtained from cell depositories or from the researchers who cloned them. But, if necessary, new clones can be prepared based on available sequence information using RT-PCR techniques. Thus, it should be easily possible to obtain all of the needed enzymes for expression or overexpression.

Another way of finding suitable enzymes/proteins for use in the invention is to consider other enzymes with the same EC number, since these numbers are assigned based on the reactions performed by a given enzyme. An enzyme that thus be obtained, e.g., from AddGene or from the author of the work describing that enzyme, and tested for functionality as described herein.

Understanding the inherent degeneracy of the genetic code allows one of ordinary skill in the art to design multiple nucleotides that encode the same amino acid sequence. NCBI™ provides codon usage databases for optimizing DNA sequences for protein expression in various species. Using such databases, a gene or cDNA may be "optimized" for expression in *E. coli*, yeast, algal or other species using the codon bias for the species in which the gene will be expressed.

In calculating "% identity" the unaligned terminal portions of the query sequence are not included in the calculation. The identity is calculated over the entire length of the reference sequence, thus short local alignments with a query sequence are not relevant (e.g., % identity=number of aligned residues in the query sequence/length of reference sequence). Alignments are performed using BLAST homology alignment as described by Tatusova T A & Madden T L (1999) FEMS Microbiol. Lett. 174:247-250, and available through the NCBI website. The default parameters were used, except the filters were turned OFF.

"Operably associated" or "operably linked", as used herein, refer to functionally coupled nucleic acid or amino acid sequences.

"Recombinant" is relating to, derived from, or containing genetically engineered material. In other words, the genome was intentionally manipulated by the hand-of-man in some way.

"Reduced activity" or "inactivation" is defined herein to be at least a 75% reduction in protein activity, as compared with an appropriate control species (e.g., the wild type gene in the same host species). Preferably, at least 80, 85, 90, 95% reduction in activity is attained, and in the most preferred embodiment, the activity is eliminated (100%). Proteins can be inactivated with inhibitors, by mutation, or by suppression of expression or translation, by knock-out, by adding stop codons, by frame shift mutation, and the like.

By "null" or "knockout" what is meant is that the mutation produces undetectable active protein. A gene can be completely (100%) reduced by knockout or removal of part of all of the gene sequence. Use of a frame shift mutation, early stop codon, point mutations of critical residues, or deletions or insertions, and the like, can also completely inactivate (100%) gene product by completely preventing transcription and/or translation of active protein. All null mutants herein are signified by Δ.

"Overexpression" or "overexpressed" is defined herein to be at least 150% of protein activity as compared with an appropriate control species, or any expression in a species that lacks the protein altogether. Preferably, the activity is increased 100-500%. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or up-regulating the endogenous gene, and the like. All overexpressed genes or proteins are signified herein by "+".

In certain species it is possible to genetically engineer the endogenous protein to be overexpressed by changing the regulatory sequences or removing repressors. However, overexpressing the gene by inclusion on selectable plasmids that exist in hundreds of copies in the cell may be preferred due to its simplicity and ease of exerting externals controls, although permanent modifications to the genome may be preferred in the long term for stability reasons.

The term "endogenous" means that a gene originated from the species in question, without regard to subspecies or strain, although that gene may be naturally or intentionally mutated, or placed under the control of a promoter that results in overexpression or controlled expression of said gene. Thus, genes from Clostridia would not be endogenous to *Escherichia*, but a plasmid expressing a gene from *E. coli* or would be considered to be endogenous to any genus of *Escherichia*, even though it may now be overexpressed.

"Wild type" means that the protein is completely functional and its amino acid sequence has not substantively changed from that found in nature, although silent mutations are possible, and even likely.

"Native" means that a protein or gene is from the host species.

"Expression vectors" are used in accordance with the art accepted definition of a plasmid, virus or other propagatable sequence designed for protein expression in cells. There are thousands of such vectors commercially available, and typically each has an origin of replication (ori); a multiple cloning site; a selectable marker; ribosome binding sites; a promoter and often enhancers; and the needed termination sequences. Most expression vectors are inducible, although constitutive expression vectors also exist.

As used herein, "inducible" means that gene expression can be controlled by the hand-of-man, by adding e.g., a ligand to induce expression from an inducible promoter. Exemplary inducible promoters include the lac operon inducible by IPTG, the yeast AOX1 promoter inducible with methanol, the strong LAC4 promoter inducible with lactate, and the like. Low level of constitutive protein synthesis may still occur even in expression vectors with tightly controlled promoters.

As used herein, an "integrated sequence" means the sequence has been integrated into the host genome, as opposed to being maintained on an expression vector. It will still be expressible, and preferably is inducible as well.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
|---|---|
| AAT | acetate-CoA transferase (E.C. 2.8.3.8) |
| AceA | Isocitrate lyase; E.C. 4.1.3.1; EG10022(EcoCyc) or POA9G6 (UniProt) |
| AceB | Malate synthase A |
| At GLYR+ | overexpression of a glyoxylate reductase from *Arabidopsis thaliana* |
| Bs fabH+ | overexpression of a β-ketoacyl-ACP synthase III from *bacillus subtilis* |
| Ec IL+ | overexpression of an isocitrate lyase from *E. coli* MG1655 |
| FA | Fatty acid |
| FABH | β-ketoacyl-ACP synthase III aka KASIII |
| FAS | Fatty acid synthesis |
| GLYR | glyoxylate reductase |
| icd | isocitrate dehydrogenase |
| IL | isocitrate lyase |
| KASIII | β-ketoacyl-ACP synthase III |
| PAL | beta-alanyl-CoA ammonia-lyase (EC 4.3.1.6) e.g., Q6KC22 from *Clostridium propionicum* |
| PAND | aspartate 1-decarboxylase; E.C. 4.1.1.11; EG11747 (EcoCyc) or POA790 (UniProt) |

-continued

| ABBREVIATION | TERM |
|---|---|
| prpE | propionyl-CoA synthetase (EC: 6.2.1.17) also known as propionate CoA ligase |
| Pyc | pyruvate carboxylase (E.C. 6.4.1.1) |
| Rc TE+ | overexpression of acyl-ACP thioesterase from *Ricinus communis* |
| Sa fabH+ | overexpression of a β-ketoacyl-ACP synthase III from *Staphylococcus aureus* |
| Se prpE+ | overexpression of a propionyl-CoA synthetase from *Salmonella enterica* |
| TE | acyl-ACP thioesterase |
| ΔaceB | deactivation or deletion of malate synthase A, aceB |
| Δicd | deactivation or deletion of isocitrate dehydrogenase |

BRIEF DESCRIPTION OF THE DRAWINGS

FIG. 4 shows the scheme of the disclosure. Strictly speaking, the donor involved in the condensation reaction is malonyl-ACP, but it is derived from acetyl-CoA, as shown here.

FIG. 5 displays a partial listing of available KASIII sequences.

FIG. 6 is a partial listing of embodiments, anyone or more of which can be combined with any other one or more.

DETAILED DESCRIPTION

Figure 1:
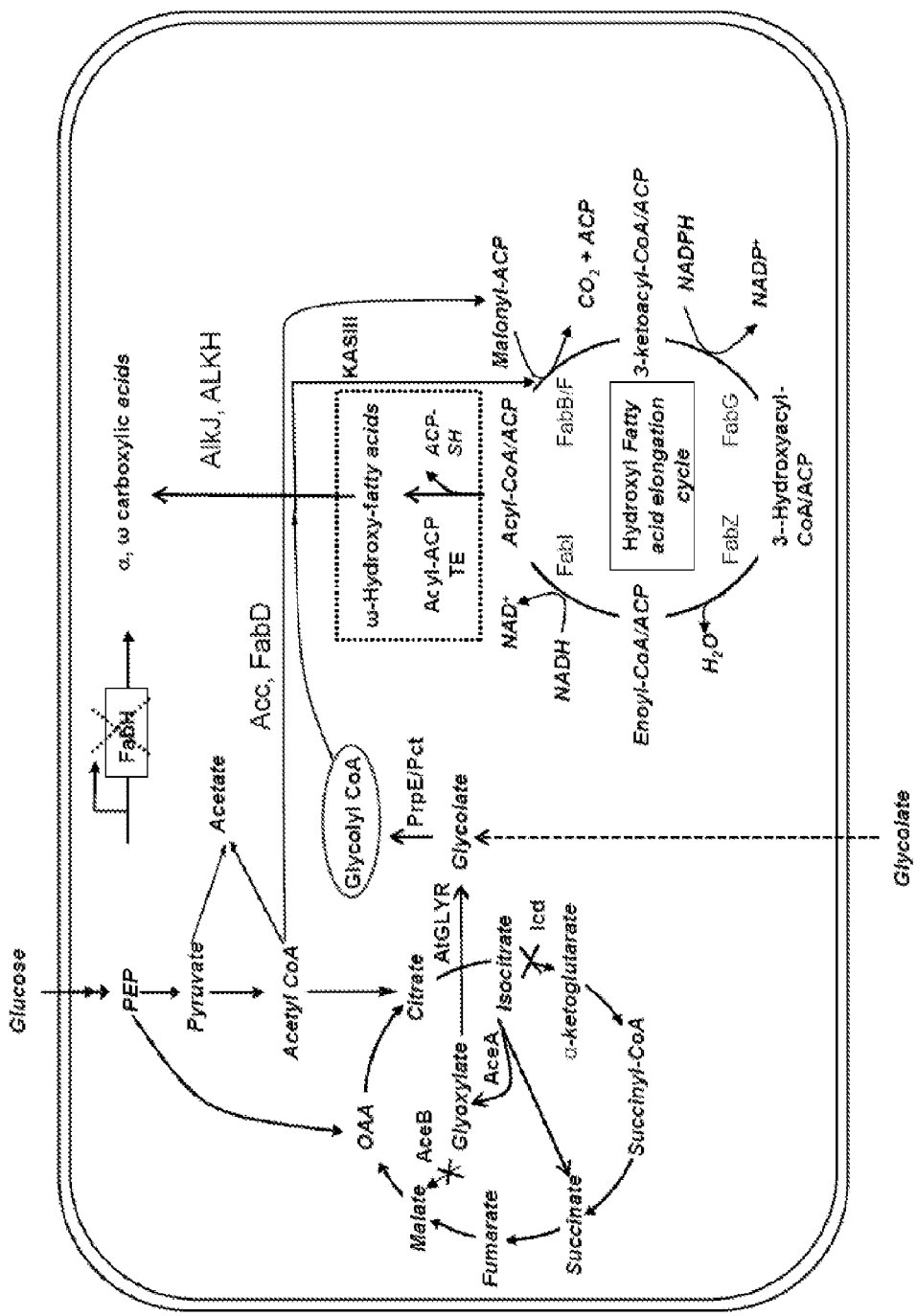
FIG. 1. Schematic diagram showing the genetically engineered biosynthetic pathway of hydroxy fatty acid and dicarboxylic fatty acid.
Figure 2:
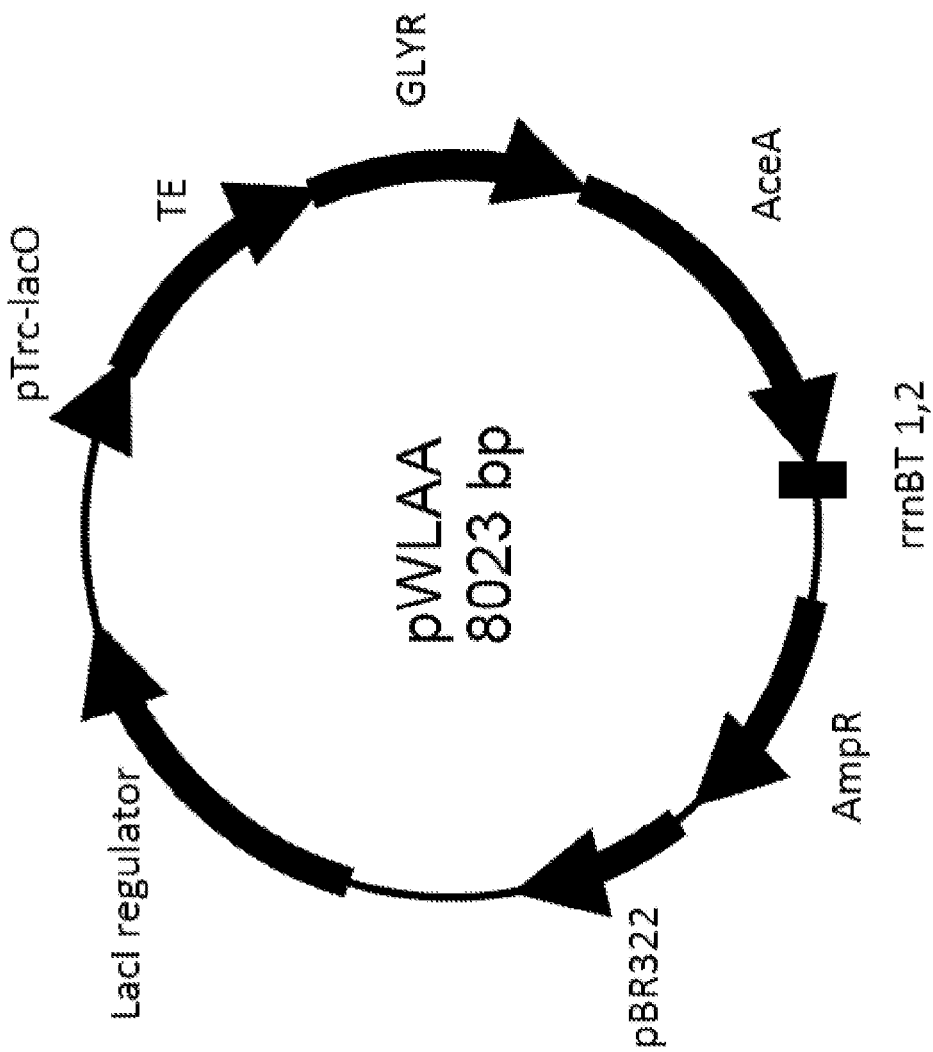
FIG. 2. Schematic diagrams of the plasmid pWLAA with TE, GLYR and AceA overexpression. TE: acyl ACP thioesterase from *Ricinus communis*; GLYR: glyoxylate reductase from *Arabidopsis thaliana*; AceA: isocitrate lyase from *Escherichia coli* MG1655; pTrc-lacO, trc promoter without lacO binding site; pTrc, trc promoter; lacI: lac operon repressor; AmpR, ampicillin resistant gene; rrnBT 1,2, transcriptional terminator of rrnB.

The specification in its entirety is to be treated as providing a variety of details that can be used interchangeably with other details, as the specification would be of inordinate length if one were to list every possible combination of genes/vectors/enzymes/hosts that can be made to enable FAS of omega functionalized fatty acids or derivatives thereof.

The invention provides a novel method of producing alpha-omega bifunctional fatty acids of various carbon chain lengths using engineered microbial from renewable carbon sources. Various constructs have been engineered and C6-16 fatty acids were successfully produced from these constructs.

16-Hydroxyhexanoic Acid with Added Glycolate

Omega-hydroxy fatty acid can be produced by providing a primer precursor to the engineered strains that can first activate this precursor by converting it to the active acyl-CoA form, and then incorporate the activated primer into the fatty acid synthesis cycle. Finally an acyl-ACP thioesterase will be used to release the free omega-hydroxy fatty acid.

Glycolate was used as the priming precursor in this proof-of-concept experiment. Three engineered strains were studied. The strain ML103 (pWL1T, pBAD33) harbors a plasmid pWL1T carrying an acyl-ACP thioesterase from *Ricinus communis* under a constitutive promoter and a cloning vector pBAD33 as the control. The second strain ML103 (pWL1T, pBHE2) also harbors the same plasmid pWL1T carrying an acyl-ACP thioesterase from *Ricinus communis* and a plasmid pBHE2 carrying a β-ketoacyl-ACP synthase III or (KASIII) from *Staphylococcus aureus* and a propionyl-CoA synthetase (to activate the glycolate) from *Salmonella enterica* in pBAD33. The other strain ML103 (pWL1T, pBHE3) is similar to the ML103 (pWL1T, pBHE2) but carrying a β-ketoacyl-ACP synthase III from *Bacillus subtilis*.

A seed culture was prepared by inoculating a single colony from a freshly grown plate in 5 mL of LB medium in an orbital shaker (New Brunswick Scientific, New Jersey, USA) operated overnight at 250 RPM and 37° C. A secondary preculture was prepared by inoculating 0.5 mL seed culture to a 250-mL flask containing 50 mL LB medium and incubating at 30° C. and 250 RPM for 9 h.

The cells were harvested aseptically by centrifugation at 3,300×g for 5 min, and resuspended in the appropriate volume of fresh fermentation medium which was calculated based on the inoculation size of 10%. LB medium was supplemented with 15 g/L of glucose and with or without the omega-functionalized primer, in this case glycolic acid (2.5 g/L or 5 g/L). The initial pH was set to be 7.5.

All of the media were supplemented with 100 mg/L ampicillin and 34 mg/L chloramphenicol. The expression of the prpE and fabH on plasmid pBHE2 and pBHE3 was induced by 10 mM arabinose. The cells were then cultivated in an orbital shake operated at 250 RPM and 30° C. Samples were taken at 24, 48 and 72 h for hydroxy fatty acids, fatty acids and extracellular metabolite analysis. All experiments were carried out in triplicate.

The ability of the engineered strain to incorporate the primer precursor-glycolate—into the fatty acid synthesis cycle to produce 16-hydroxyhexanoic acid was demonstrated in Table 1. The control strain did not produce any detectable quantity of hydroxyl fatty acid. Both strains, ML103 (pWL1T, pBHE2) and ML103 (pWL1T, pBHE3), produce significant quantities of omega hydroxy fatty acids (Table 1). The strain ML103 (pWL1T, pBHE2) produced more than 425 mg/L of omega hydroxy fatty acids with 5 g/L of glycolate addition (Table 1).

Figure 3:
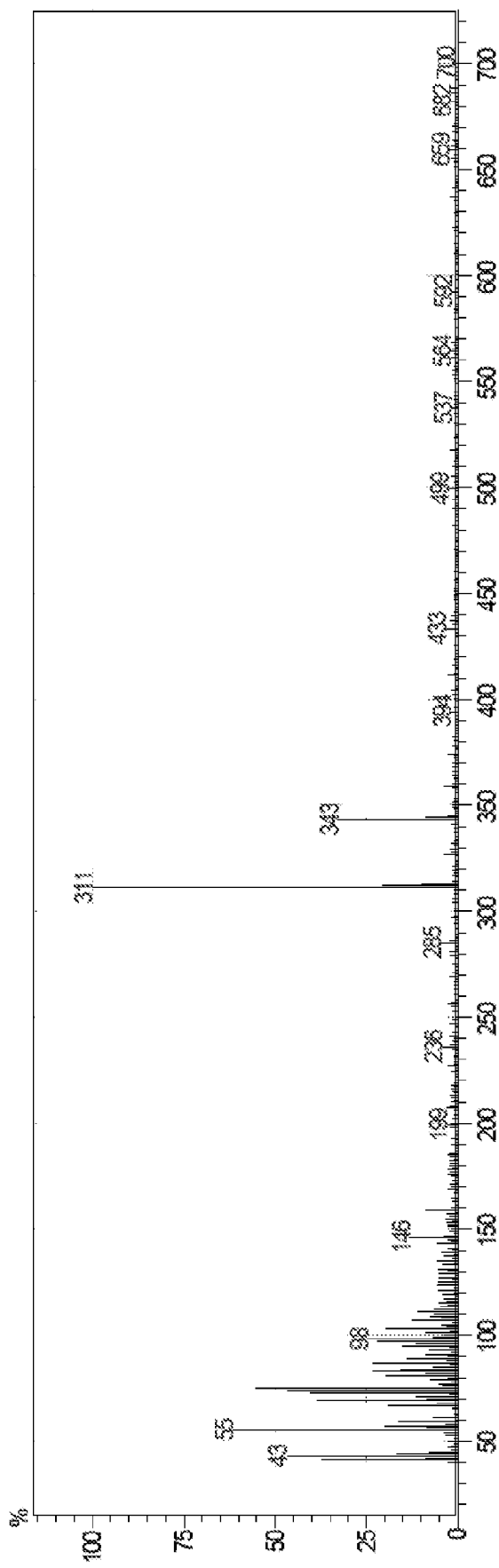
FIG. 3. Mass spectrum of the fragmentation patterns of derivatized 16-hydroxyhexadecanoic acid of sample.

The mass spectrum of the fragmentation patterns of derivatized 16-hydroxyhexadecanoic acid of sample is shown in FIG. 3, which is verified with that from the NIST/EPA/NIH Spectral Library.

Note: the ΔfadD mutant was for convenience only and is not essential, although it is beneficial. The protein FadD encodes a long-chain fatty acyl coenzyme A (acyl-CoA) ligase that is postulated to activate exogenous long-chain fatty acids by acyl-CoA ligation concomitant with transport across the cytoplasmic membrane. Thus, the mutant produces higher amounts of fatty acids because this null mutant reduces beta oxidation of fats.

TABLE 1

Production of long chain length omega- hydroxy fatty acid using exogenous glycolate

| Strains | Relevant phenotype | Glycolate addition (g/L) | Time (h) | Cell density (OD$_{600}$) | Glucose consumed (mM) | ω-hydroxyhexadecanoic acid (mg/L) |
|---|---|---|---|---|---|---|
| ML103 (pWL1T, pBAD33) | ΔfadD Rc TE⁺ | 2.5 | 24 | 9.27 ± 0.15 | 47.2 ± 1.78 | ND |
| | | | 48 | 4.93 ± 0.14 | 77.6 ± 1.67 | ND |
| | | | 72 | 4.22 ± 0.13 | 86.5 ± 1.11 | ND |
| ML103 (pWL1T, pBAD33) | ΔfadD Rc TE⁺ | 5.0 | 24 | 10.3 ± 0.11 | 45.1 ± 0.76 | ND |
| | | | 48 | 5.46 ± 0.31 | 78.4 ± 2.31 | ND |
| | | | 72 | 3.97 ± 0.14 | 85.3 ± 0.40 | ND |
| ML103 (pWL1T, pBHE2) | ΔfadD Rc TE⁺ Sa fabH⁺ Se prpE⁺ | 2.5 | 24 | 4.81 ± 0.09 | 31.6 ± 1.79 | 171 ± 2.07 |
| | | | 48 | 6.14 ± 0.16 | 50.0 ± 1.13 | 271 ± 7.6 |
| | | | 72 | 8.81 ± 0.36 | 61.4 ± 0.34 | 288 ± 10.6 |
| ML103 (pWL1T, pBHE2) | ΔfadD Rc TE⁺ Sa fabH⁺ Se prpE⁺ | 5.0 | 24 | 5.65 ± 0.11 | 26.4 ± 0.41 | 191 ± 4.46 |
| | | | 48 | 7.09 ± 0.36 | 46.8 ± 1.03 | 386 ± 5.82 |
| | | | 72 | 10.3 ± 0.24 | 64.5 ± 0.67 | 428 ± 6.06 |
| ML103 (pWL1T, pBHE3) | ΔfadD Rc TE⁺ Bs fabH⁺ Se prpE⁺ | 2.5 | 24 | 6.59 ± 0.12 | 39.6 ± 0.60 | 158 ± 3.06 |
| | | | 48 | 8.44 ± 0.09 | 55.5 ± 0.58 | 257 ± 0.88 |
| | | | 72 | 9.94 ± 0.10 | 66.0 ± 0.17 | 279 ± 4.23 |
| ML103 (pWL1T, pBHE3) | ΔfadD Rc TE⁺ Bs fabH⁺ Se prpE⁺ | 5.0 | 24 | 7.30 ± 0.38 | 34.4 ± 1.04 | 179 ± 2.75 |
| | | | 48 | 9.45 ± 0.40 | 54.2 ± 0.72 | 309 ± 1.43 |
| | | | 72 | 10.5 ± 0.17 | 71.6 ± 0.79 | 332 ± 2.44 |

ND: not detected.
Rc_TE⁺: overexpression of acyl-ACP thioesterase from *Ricinus communis* under a constitutive promoter system in a modified pTrc99a cloning vector
Sa fabH⁺: overexpression of a β-ketoacyl-ACP synthase III from *Staphylococcus aureus* in pBAD33
Se prpE⁺: overexpression of a propionyl-CoA synthetase from *Salmonella enterica*
Bs fabH⁺: overexpression of a β-ketoacyl-ACP synthase III from *Bacillus subtilis* in pBAD33

Omega-Hydroxytetradecanoic Acid from Glycolate

Glycolate was used as the primer precursor in this experiment, which changed the TE to make a shorter omega functionalized fat. Two engineered strains were studied. The strain ML103 (pXZM12, pBHE2) also harbors the plasmid pXZM12 carrying an acyl-ACP thioesterase from *Umbellularia californica* and a plasmid pBHE2 carrying a β-ketoacyl-ACP synthase III from *Staphylococcus aureus* and a propionyl-CoA synthetase from *Salmonella enterica* in pBAD33. The other strain ML103 (pXZM12, pBHE3) is similar to the ML103 (pXZM12, pBHE2) but carrying a β-ketoacyl-ACP synthase III from *bacillus subtilis*.

The seed culture and secondary preculture were prepared as described. The cells were harvested and inoculated at 10% as described in LB, pH 7.5, with 15 g/L of glucose and with or without glycolic acid (2.5 g/L or 5 g/L). All of the media were supplemented with 100 mg/L ampicillin and 34 mg/L chloramphenicol. The expression of TE from U. *Californica* (pXZM12) was induced by the addition of isopropyl-β-D-thiogalactopyranoside (IPTG) to the final concentration of 200 μM. The expression of the prpE and fabH on plasmid pBHE2 and pBHE3 was induced by 10 mM arabinose.

The cells were then cultivated in an orbital shaker operated at 250 RPM and 30° C. Samples were taken at 24, 48 and 72 h for hydroxy fatty acids, fatty acids and extracellular metabolite analysis. All experiments were carried out in triplicate.

The ability of the engineered strain to incorporate the primer precursor—glycolate—into the fatty acid synthesis cycle to produce ω-hydroxyhexanoic acid was demonstrated in Table 2. Both strains, ML103 (pXZM12, pBHE2) and ML103 (pXZM12, pBHE3), produce significant quantities of omega hydroxy fatty acids (Table 2). The strain ML103 (pXZM12, pBHE2) produced more than 240 mg/L of omega hydroxy fatty acids with 5 g/L of glycolate addition (Table 2).

TABLE 2

Production of medium chain length (C14) omega-hydroxy fatty acid using exogenous glycolate

| Strains | Relevant phenotype | Glycolate Addition (g/L) | Time (h) | Cell density (OD$_{600}$) | Glucose consumed (mM) | ω-hydroxytetradecanoic acid (mg/L) |
|---|---|---|---|---|---|---|
| ML103 (pXZM12, pBHE2) | ΔfadD Ua_TE⁺ Sa fabH⁺ Se prpE⁺ | 2.5 | 24 | 5.22 ± 0.21 | 35.8 ± 1.42 | 72.4 ± 2.54 |
| | | | 48 | 7.36 ± 0.14 | 55.6 ± 1.21 | 161 ± 9.88 |
| | | | 72 | 9.11 ± 0.25 | 66.2 ± 0.68 | 196 ± 7.45 |
| ML103 (pXZM12, pBHE2) | ΔfadD Ua_TE⁺ Sa fabH⁺ Se prpE⁺ | 5.0 | 24 | 5.35 ± 0.16 | 28.4 ± 0.55 | 106 ± 3.36 |
| | | | 48 | 7.68 ± 0.22 | 48.2 ± 1.21 | 189 ± 8.90 |
| | | | 72 | 9.72 ± 0.31 | 65.1 ± 0.88 | 248 ± 11.7 |
| ML103 (pXZM12, | ΔfadD Ua_TE⁺ | 2.5 | 24 | 6.15 ± 0.11 | 36.2 ± 0.69 | 68.5 ± 4.2 |
| | | | 48 | 8.23 ± 0.07 | 58.9 ± 0.42 | 112 ± 8.65 |

TABLE 2-continued

Production of medium chain length (C14) omega-hydroxy fatty acid using exogenous glycolate

| Strains | Relevant phenotype | Glycolate Addition (g/L) | Time (h) | Cell density (OD$_{600}$) | Glucose consumed (mM) | ω-hydroxytetradecanoic acid (mg/L) |
|---|---|---|---|---|---|---|
| pBHE3) | Bs fabH$^+$ Se prpE$^+$ | | 72 | 9.96 ± 0.22 | 70.1 ± 0.21 | 156 ± 7.93 |
| ML103 (pXZM12, pBHE3) | ΔfadD Ua_TE$^+$ Bs fabH$^+$ Se prpE$^+$ | 5.0 | 24 48 72 | 6.84 ± 0.25 8.85 ± 0.32 10.6 ± 0.16 | 26.3 ± 1.56 51.8 ± 0.65 67.4 ± 0.88 | 90.4 ± 4.36 172 ± 7.82 216 ± 9.91 |

Ua_TE$^+$: overexpression of acyl-ACP thioesterase from *Umbellularia californica* under a constitutive promoter system in a modified pTrc99a cloning vector
Sa fabH$^+$: overexpression of a β-ketoacyl-ACP synthase III from *Staphylococcus aureus* in pBAD33
Se prpE$^+$: overexpression of a propionyl-CoA synthetase from *Salmonella enterica*
Bs fabH$^+$: overexpression of a β-ketoacyl-ACP synthase III from *bacillus subtilis* in pBAD33

Engineered Strains Producing Glycolate

In the above proof of concept experiments, glycolate was provided to the cells for use as a primer precursor. However, strains can be built to provide their own primers and/or precursors, and this experiment demonstrates proof of concept for microbes engineered to make glycolate.

Several strains were designed, constructed and tested for their ability to produce glycolate in vivo from renewable carbon source such as glucose. The design is based on first producing glyoxylate from glucose using the glyoxylate bypass pathway and then converting glyoxylate to glycolate using the enzyme glyoxylate reductase.

Several metabolic engineering approaches were used to further divert the carbon flux to glyoxylate; these include the overexpression of isocitrate lyase, and inactivation of both malate synthase and isocitrate dehydrogenase.

The control strain ML013(pWL1T) did not produce any detectable glycolate. However, the strain ML103 (pWLA), carrying the glyoxylate reductase from *A. thaliana* is capable of producing 186 mg/L of glycolate (Table 3). Glycolate production further increased to 304 mg/L with the overexpression of both glyoxylate reductase and isocitrate lyase.

Using the malate synthase mutant strain, DW101, as the host strain further increases the glycolate production. The strain DW101 (pWLA) with overexpression of glyoxylate reductase from *A. thaliana* produced 633 mg/L of glycolate while the strain DW101 (pWLAA) with overexpression of glyoxylate reductase and isocitrate lyase produced as high as 939 mg/L of glycolate.

The malate synthase and isocitric dehydrogenase double mutant strain, DW102, produces even higher levels of glycolate. The DW102 (pWLA) and DW102 (pWLAA) produced 819 mg/L and 1204 mg/L of glycolate, respectively. This set of experiments demonstrated that glycolate can be produced at high levels with the engineered strains.

TABLE 3

Production of glycolate by engineered strains

| Strains | Relevant phenotype | Time (h) | Cell density (OD$_{600}$) | Glucose consumed (mM) | Acetate (mM) | glycolate (mg/L) |
|---|---|---|---|---|---|---|
| ML103 (pWL1T) | ΔfadD Rc_TE$^+$ | 24 48 72 | 7.76 ± 0.30 5.41 ± 0.17 5.08 ± 0.12 | 43.2 ± 0.84 74.8 ± 0.57 85.4 ± 0.33 | 12.7 ± 0.34 24.0 ± 1.74 8.60 ± 0.30 | ND ND ND |
| ML103 (pWLA) | ΔfadD Rc_TE$^+$ At GLYR$^+$ | 24 48 72 | 8.21 ± 0.11 6.00 ± 0.12 4.47 ± 0.15 | 40.8 ± 2.26 69.5 ± 1.80 80.1 ± 0.85 | 14.6 ± 0.43 23.2 ± 0.46 12.4 ± 0.03 | ND ND 186 ± 7.39 |
| ML103 (pWLAA) | ΔfadD Rc_TE$^+$ At GLYR$^+$ Ec IL$^+$ | 24 48 72 | 5.68 ± 0.25 6.15 ± 0.10 5.01 ± 0.07 | 31.5 ± 1.52 58.4 ± 0.52 69.7 ± 0.63 | 15.5 ± 0.62 26.8 ± 0.98 14.5 ± 0.30 | ND 121 ± 4.49 304 ± 7.90 |
| DW101 (pWLA) | ΔfadD ΔaceB Rc_TE$^+$ At GLYR$^+$ | 24 48 72 | 4.34 ± 0.13 5.43 ± 0.31 3.40 ± 0.13 | 27.9 ± 0.44 54.5 ± 0.68 67.4 ± 0.29 | 14.4 ± 0.36 45.2 ± 0.10 57.0 ± 0.81 | ND 212 ± 8.21 633 ± 8.85 |
| DW101 (pWLAA) | ΔfadD ΔaceB Rc_TE$^+$ At GLYR$^+$ Ec IL$^+$ | 24 48 72 | 4.18 ± 0.06 4.65 ± 0.04 3.14 ± 0.15 | 30.2 ± 1.00 51.5 ± 0.94 67.5 ± 0.97 | 17.9 ± 0.55 42.9 ± 0.48 56.0 ± 0.53 | 385 ± 6.12 605 ± 17.0 939 ± 10.1 |
| DW102 (pWLA) | ΔfadD ΔaceB Δicd Rc_TE$^+$ At GLYR$^+$ | 24 48 72 | 4.56 ± 0.22 4.82 ± 0.11 3.59 ± 0.13 | 25.8 ± 0.94 46.7 ± 0.63 61.9 ± 0.38 | 20.9 ± 0.54 46.0 ± 0.60 60.6 ± 0.74 | 324 ± 14.2 556 ± 13.4 819 ± 9.45 |

TABLE 3-continued

Production of glycolate by engineered strains

| Strains | Relevant phenotype | Time (h) | Cell density ($OD_{600}$) | Glucose consumed (mM) | Acetate (mM) | glycolate (mg/L) |
|---|---|---|---|---|---|---|
| DW102 (pWLAA) | ΔfadD ΔaceB Δicd Rc_TE+ At GLYR+ Ec IL+ | 24 48 72 | 3.54 ± 0.11 4.10 ± 0.22 4.36 ± 0.14 | 21.9 ± 0.48 40.3 ± 0.46 55.1 ± 0.71 | 18.2 ± 0.24 46.0 ± 0.67 62.6 ± 0.66 | 318 ± 7.34 1012 ± 26.4 1206 ± 38.5 |

ND: not detected.
Rc_TE+: overexpression of acyl-ACP thioesterase from *Ricinus communis* under a constitutive promoter system in a modified pTrc99a cloning vector
At GLYR+: overexpression of a glyoxylate reductase from *Arabidopsis thaliana*
Ec IL+: overexpression of an isocitrate lyase from *E. coli* MG1655
ΔaceB: deactivation or deletion of malate synthase A, aceB
Δicd: deactivation or deletion of isocitrate dehydrogenase De Novo Hydroxy Fatty Acid from Glucose The above experiments proved that we can design strains to make omega hydroxy fats of varying length with added primer precursor. We also showed that we could add a pathway to make the precursor in vivo. These next experiments provide proof-of-concept that both concepts function together, to make omega-hydroxy fats de novo from a carbon source, such as glucose.

In this experiment as an example, the de novo production of hydroxy fatty acid, specifically w-hydroxyhexadecanoic (c16) acid, from glucose was demonstrated using the engineered strains.

Three engineered strains were studied. The control strain DW102 (pTrc99A, pBAD33) harbors two cloning vectors pTrc99a and pBAD33.

The second strain DW102 (pWLAA, pBHE2) harbors two plasmids; plasmid pWLAA carries an acyl-ACP thioesterase from *Ricinus communis*, a glyoxylate reductase from *Arabidopsis thaliana* and an isocitrate lyase from *E. coli* MG1655 while plasmid pBHE2 carries a β-ketoacyl-ACP synthase III from *Staphylococcus aureus* and a propionyl-CoA synthetase from *Salmonella enterica*.

The third strain DW102 (pWLAA, pBHE3) also harbors two plasmids which include the same plasmid pWLAA and plasmid pBHE3 carrying a β-ketoacyl-ACP synthase III from *bacillus subtilis* and a propionyl-CoA synthetase from *Salmonella enterica*.

The experiments were as described above, and the expression of the prpE and fabH on plasmid pBHE2 and pBHE3 was induced by 10 mM arabinose, and the expression of the TE was induced by IPTG. Isocitrate lyase was induced with IPTG.

The control strain, DW102 (pTrc99A, pBAD33) did not show any detectable co-hydroxyhexadecanoic acid. Both DW102 (pWLAA, pBHE2) and DW102 (pWLAA, pBHE3) produced more than 300 mg/L of hydroxyhexadecanoic (C16) acid in 72 h (Table 4). These results clearly demonstrate the ability of the engineered strain to produce hydroxyl fatty acids from glucose.

TABLE 4

De novo hydroxy fatty acid production from glucose

| Strains | Relevant phenotype | Time (h) | Cell density ($OD_{600}$) | Glucose consumed (mM) | Acetate (mM) | ω-hydroxyhexadecanoic acid (mg/L) |
|---|---|---|---|---|---|---|
| DW102 (pTrc99A, pBAD33) | ΔfadD | 24 48 72 | 4.37 ± 0.25 5.35 ± 0.27 7.52 ± 0.24 | 28.7 ± 0.57 43.4 ± 0.20 54.2 ± 1.63 | 17.9 ± 0.73 41.3 ± 0.80 60.7 ± 0.50 | ND ND ND |
| DW102 (pWLAA, pBHE2) | ΔfadD ΔaceB Δicd Rc_TE+ At GLYR+ Sa fabH+ Se prpE+ | 24 48 72 | 4.11 ± 0.19 5.68 ± 0.06 6.47 ± 0.15 | 26.4 ± 0.65 32.6 ± 1.27 39.0 ± 0.93 | 14.6 ± 0.43 36.3 ± 0.48 43.7 ± 1.10 | 188 ± 4.73 296 ± 6.86 342 ± 13.6 |
| DW102 (pWLAA, pBHE3) | ΔfadD ΔaceB Δicd Rc_TE+ At GLYR+ | 24 48 72 | 3.80 ± 0.15 4.48 ± 0.26 5.25 ± 0.07 | 24.05 ± 0.83 30.42 ± 0.95 35.70 ± 0.15 | 16.8 ± 0.79 34.9 ± 1.88 46.7 ± 0.57 | 170 ± 2.09 288 ± 7.16 329 ± 12.0 |

TABLE 4-continued

De novo hydroxy fatty acid production from glucose

| Strains | Relevant phenotype | Time (h) | Cell density (OD$_{600}$) | Glucose consumed (mM) | Acetate (mM) | ω-hydroxyhexadecanoic acid (mg/L) |
|---|---|---|---|---|---|---|
| | Ec IL$^+$ Bs fabH$^+$ Se prpE$^+$ | | | | | |

Rc_TE$^+$: overexpression of acyl-ACP thioesterase from *Ricinus communis* under a constitutive promoter system in a modified pTrc99a cloning vector
At GLYR$^+$: overexpression of a glyoxylate reductase from *Arabidopsis thaliana*
Ec IL$^+$: overexpression of an isocitrate lyase from *E. coli* MG1655
Sa fabH$^+$: overexpression of a β-ketoacyl-ACP synthase III from *Staphylococcus aureus* in pBAD33
Se prpE$^+$: overexpression of a propionyl-CoA synthetase from *Salmonella enterica*
Bs fabH$^+$: overexpression of a β-ketoacyl-ACP synthase III from *bacillus subtilis* in pBAD33
ΔaceB: deactivation or deletion of malate synthase A, aceB
Δicd: deactivation or deletion of isocitrate dehydrogenase Amino Fats with Beta-Alanine Added Beta-alanine is used as the priming molecule in this experiment to produce amino fatty acids. Three engineered strains will be studied. The strain ML103(pWL1T, pBAD33) harbors a plasmid pWL1T carrying an acyl-ACP thioesterase from *Ricinus communis* under a constitutive promoter and a cloning vector pBAD33 as the control. The second strain ML103 (pWL1T, pBHE2) also harbors the same plasmid pWL1T carrying an acyl-ACP thioesterase from *Ricinus communis* and a plasmid pBHE2 carrying a β-ketoacyl-ACP synthase III from *Staphylococcus aureus* and a propionyl-CoA synthetase from *Salmonella enterica* in pBAD33. The other strain ML103 (pWL1T, pBHE3) is similar to the ML103 (pWL1T, pBHE2), but carrying a β-ketoacyl-ACP synthase III from *bacillus subtilis*.

The seed culture is prepared by inoculating a single colony from a freshly grown plate in 5 mL of LB medium in an orbital shaker (New Brunswick Scientific, New Jersey, USA) is operated overnight at 250 RPM and 37° C. The secondary preculture is prepared by inoculating 0.5 mL seed culture to a 250-mL flask containing 50 mL LB medium and incubating at 30° C. and 250 RPM for 9 h.

The cells are harvested aseptically by centrifugation at 3,300×g for 5 min, and resuspended in the appropriate volume of fresh fermentation medium which is calculated based on the inoculation size of 10%. LB medium is supplemented with 15 g/L of glucose and with or without beta-alanine acid (2.5 g/L or 5 g/L) as the primer precursor. The initial pH is set to be 7.5.

All of the media are supplemented with 100 mg/L ampicillin and 34 mg/L chloramphenicol. The expression of the prpE and fabH on plasmid pBHE2 and pBHE3 is induced by 10 mM arabinose.

The cells are then cultivated in an orbital shake is operated at 250 RPM and 30° C. Samples are taken at 24, 48 and 72 h for amino fatty acids, fatty acids and extracellular metabolite analysis. All experiments are carried out in triplicate.

Amino Fats with Beta-Alanine In Vivo

Beta-alanine produced in vivo is used as the priming molecule in this experiment. Beta alanine overproducing strains, named KSBA100, with overexpression of pyruvate carboxylase (Pyc), aspartate aminotransferase (AAT) and aspartate decarboxylase (PAND) from various sources are constructed.

Three engineered strains will be studied in this experiment to generate amino fatty acids. The strain KSBA100 (pWL1T, pBAD33) harbors the genes encoded for Pyc, AAT, PAND and TE from *Ricinus communis* and a cloning vector pBAD33 as the control. The second strain KSBA100 (pWL1T, pBHE2) also harbors the same set of genes encoded for Pyc, AAT, PAND and TE from *Ricinus communis* and a plasmid pBHE2 carrying a β-ketoacyl-ACP synthase III from *Staphylococcus aureus* and a propionyl-CoA synthetase from *Salmonella enterica* in pBAD33. The other strain KSBA100 (pWL1T, pBHE3) is similar to the KSBA100 (pWL1T, pBHE2) but carrying a β-ketoacyl-ACP synthase III from *Bacillus subtilis*.

The experiments were as described above, except a pathway is added to synthesize beta-alanine in vivo from glucose instead of externally added beta-alanine, and thus no beta alanine need be added to the culture medium.

Omega-Unsaturated Fatty Acids with Acrylic Acid

Externally added acrylic acid is used as the priming molecule in this experiment to produce omega unsaturated fatty acids. Three engineered strains will be studied. The strain ML103 (pWL1T, pBAD33) harbors a plasmid pWL1T carrying an acyl-ACP thioesterase from *Ricinus communis* under a constitutive promoter and a cloning vector pBAD33 as the control. The second strain ML103 (pWL1T, pBHE2) also harbors the same plasmid pWL1T carrying an acyl-ACP thioesterase from *Ricinus communis* and a plasmid pBHE2 carrying a β-ketoacyl-ACP synthase III from *Staphylococcus aureus* and a propionyl-CoA synthetase from *Salmonella enterica* in pBAD33. The other strain ML103 (pWL1T, pBHE3) is similar to the ML 103 (pWL1T, pBHE2) but carrying a β-ketoacyl-ACP synthase III from *bacillus subtilis*.

The experiments were as described above, except the priming precursor, acrylic acid, has an unsaturated bond, and is added to the medium instead of glycolate.

Omega-Unsaturated Fats with Propenoyl-CoA In Vivo

Beta-alanine produced in vivo is used as the priming molecule in this experiment to produce omega unsaturated fatty acids. Beta alanine overproducing strains, named KSBA100, with overexpression pyruvate carboxylase (Pyc), aspartate aminotransferase (AAT) and aspartate decarboxylase (PAND) from various sources constructed above will be used. In addition, beta-alanyl-CoA ammonia-lyase (PAL) will be overexpressed to convert beta-alanyl-CoA to propenoyl-CoA:

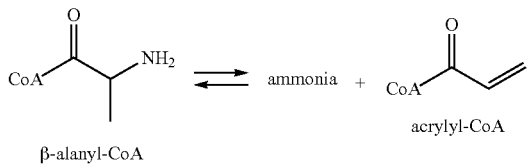

This strain is named KSPC100.

Three engineered strains will be studied. The strain KSPC100 (pWL1T, pBAD33) harbors the genes encoded for Pyc, AAT, PAND, TE from *Ricinus communis* and a cloning vector pBAD33 as the control. The second strain KSPC100 (pWL1T, pBHE2) also harbors the same set of genes encoded for Pyc, AAT, PAND, TE from *Ricinus communis* but a plasmid pBHE2 carrying a β-ketoacyl-ACP synthase III from *Staphylococcus aureus* and a propionyl-CoA synthetase from *Salmonella enterica* in pBAD33. The other strain KSPC100 (pWL1T, pBHE3) is similar to the KSPC100 (pWL1T, pBHE2) but carrying a β-ketoacyl-ACP synthase III from *bacillus subtilis*.

The experiments were as described above, except a pathway is added to synthesize acrylic acid in vivo from glucose, instead of externally added acrylic acid Alpha, Omega Dicarboxylic Acid Engineered strains with the ability to produce omega-hydroxy fatty acids are further engineered to overexpress alcohol dehydrogenase (AlkJ) and aldehyde dehydrogenase (AlkH) for the conversion of hydroxyl fatty acids to dicarboxylic acids. Hence, this strain has the relevant genotype of ΔfadD, ΔaceB, Δicd, Rc_TE+, At GLYR+, Sa fabH+, Se prpE+, alkJ+ and alkH+.

The experiments were as described above, except an additional pathway is added to convert the hydroxyl end to carboxylic acid, or to convert the hydroxyl to aldehyde if just the AlkJ is added. Although these experiments are not yet complete, this conversion has already been shown to work in other engineered strains.

Alpha, Omega Dicarboxylic Acids by Co-Culture

Engineered strains with the ability to produce omega-hydroxy fatty acids are co-cultured with strain ML103 (pAlkJH). The plasmid pALkJH carries the genes encoded for alcohol dehydrogenase (alkJ) and aldehyde dehydrogenase (alkH) for the conversion of hydroxy fatty acids to dicarboxylic acids. The use of alkJ alone will produce aldehydes, while the use of both will produce the dicarboxylates.

The seed culture is prepared by inoculating a single colony of these two strains (ML103 (pWLAA, pBHE3) and ML103(pAlkJH)) from a freshly grown plate in 5 mL of LB medium in an orbital shaker (New Brunswick Scientific, New Jersey, USA) is operated overnight at 250 RPM and 37° C. The secondary preculture is prepared by inoculating 0.5 mL seed culture to a 250-mL flask containing 50 mL LB medium and incubating at 30° C. and 250 RPM for 9 h.

The two cultures are harvested aseptically by centrifugation at 3,300×g for 5 min, and the cells are resuspended in the appropriate volume of fresh fermentation medium, which is calculated based on the inoculation size of 10%. LB medium is supplemented with 15 g/L of glucose. Optionally, glycolate (2.5 g/L or 5 g/L) will be added depending on the strains being used. The initial pH is set to be 7.5.

All of the media are supplemented with 100 mg/L ampicillin and 34 mg/L chloramphenicol. The expression of the prpE and fabH on plasmid pBHE2 and pBHE3 is induced by 10 mM arabinose.

The cells are then cultivated in an orbital shake is operated at 250 RPM and 30° C. Samples are taken at 24, 48 and 72 h for dicarboxlic acids, fatty acids and extracellular metabolite analysis. All experiments are carried out in triplicate.

Although these experiments are not yet complete, they are expected to work since we have demonstrated it before by using externally added octanoic acid.

The above experiments are repeated in *Bacillus subtilis*. The same genes can be used, especially since *Bacillus* has no significant codon bias. A protease-deficient strain like WB800N is preferably used for greater stability of heterologous protein. The *E. coli-B. subtilis* shuttle vector pMTLBS72 exhibiting full structural stability can be used to move the genes easily to a more suitable vector for *Bacillus*. Alternatively, two vectors pHT01 and pHT43 allow high-level expression of recombinant proteins within the cytoplasm. As yet another alternative, plasmids using the theta-mode of replication such as those derived from the natural plasmids pAM3 and pBS72 can be used. Several other suitable expression systems are available. Since the FAS enzymes are ubiquitous, the invention is predicted to function in *Bacillus*.

The above experiments are repeated in yeast. The same genes can be used, but it may be preferred to accommodate codon bias. Several yeast *E. coli* shuttle vectors are available for ease of the experiments. Since the FAS enzymes are ubiquitous, the invention is predicted to function in yeast, especially since yeast are already available with exogenous functional TE genes and various modified FAS pathways have also been made to run in yeast.

The following references are incorporated by reference in their entirety for all purposes.

Choi, K. H., R. J. Heath, and C. O. Rock. 2000. β-Ketoacyl-acyl carrier protein synthase III (FabH) is a determining factor in branched-chain fatty acid biosynthesis. J. Bacteriol. 182:365-370.

He, X., and K. A. Reynolds. 2002. Purification, characterization, and identification of novel inhibitors of the beta-ketoacyl-acyl carrier protein synthase III (FabH) from *Staphylococcus aureus*. Antimicrob. Agents Chemother. 46:1310-1318.

WO2000075343 Engineering B-Ketoacyl ACP Synthase For Novel Substrate Specificity US20160090576 Materials and methods for characterizing and using kasiii for production of bi-functional fatty acids.

Qiu, X, et al., Crystal structure and substrate specificity of the b-ketoacyl-acyl carrier protein synthase III (FabH) from *Staphylococcus aureus*, Protein Science (2005), 14:2087-2094 (2005).

The invention claimed is:

1. An engineered bacterial cell comprising overexpressed enzymes to produce alpha, omega-bifunctionalized products, the overexpressed enzymes including:
   i) acyl-ACP thioesterase (TE);
   ii) β-ketoacyl-ACP synthase III (KASIII) with substrate specificity for an omega functionalized-CoA primer;
   iii) a CoA synthase able to convert a primer precursor to said omega functionalized-CoA primer; and iv) optionally, reduced expression of any endogenous KASI, KASII or KASIII having a substrate preference for acetyl-CoA and propionyl-CoA,
wherein said engineered bacterial cell comprises one of the following genotypes:
a) TE+ and FabH+ and PrpE+;
b) Rc TE+ and Sa FabH+ and Se PrpE+;
c) Rc TE+ and Bs FabH+ and Se PrpE+;
d) Ua TE+ and SaFabH+ and Se PrpE+;
e) Ua TE+, Bs FabH+ and Se PrpE+;
f) any of a-e) with added IL+ and GLYR+;
g) any of a-e) with added Ec IL+ and At GLYR+;
h) any of a-e) with added IL+and GLYR+and deleted endogenous Δicd and ΔaceB,
i) any of a-e) with added Ec IL+ and At GLYR+ and deleted endogenous Δicd and ΔaceB;
j) any of a-e) with added PYC+ and AAT+ and PAND+;
k) any of a-e) with added PYC+ and AAT+ and PAND+ and PAL+;
l) any of a-k) with added alcohol dehydrogenase (AlkJ) or AlkJ and aldehyde dehydrogenase (AlkH); and
m) any of a-l) with added ΔfadD;
wherein Ec=E. coli, Re=Ricinus communis, Se=Salmonella enterica, At=Arabidopsis thaliana, Sa=Staphylococcus aureus, Bs=Bacillus subtilis, and Ua=Umbellularia californica, PrpE=propionyl-CoA synthetase, IL=isocitrate lyase, GLYR=glyoxylate reductase, PYC=pyruvate carboxylase, AAT=acetate-CoA transferase, PAND=aspartate 1-decarboxylase, PAL=bata-alanyl-CoA ammonia-lyase.

2. The bacteria cell of claim 1, wherein the omega functionalized-coA primers, the enzymes, and products are selected from:
(i) primer: glycolate; enzymes: PrpE (propionyl-CoA synthetase), FabH (KASIII), and TE (acyl-ACP thioesterase); products; ω-hydroxy fatty acids (FA);
(ii) primer: beta alanine; enzymes: PrpE, FabH and TE; products: ω-amino FA; or
(iii) primer: acrylic acid; enzymes: PrpE, FabH and TE; products: ω-unsaturated FA.

3. The bacteria cell of claim 1, further comprising:
a) overexpression of:
i) a propionyl-CoA synthetase,
ii) a glyoxylate reductase, and
iii) an isocitrate lyase; and,
b) deactivation of:
i) endogenous malate synthase A,
ii) endogenous isocitrate dehydrogenase, and
iii) endogenous acyl-CoA synthetase.

4. The bacteria cell of claim 1, further comprising overexpression of
a) pyruvate carboxylase (E.C. 6.4.1.1);
b) acetate-CoA transferase (E.C. 2.8.3.8); and,
c) aspartate 1-decarboxylase (E.C. 4.1.1.11).

5. The bacteria cell or claim 4, further comprising overexpressed beta-alanyl-CoA ammonia-lyase (EC 4.3.1.6).

6. The bacteria cell of claim 1, further including overexpression of a propionyl-CoA synthetase, overexpression of a glyoxylate reductase, overexpression of an isocitrate lyase, deactivation or deletion of endogenous malate synthase A, deactivation or deletion of endogenous isocitrate dehydrogenase, and deactivation or deletion of native acyl-CoA synthetase.

7. The bacteria cell of claim 1, wherein the KASIII is FabH from a Gram-positive bacteria.

8. The bacteria cell of claim 1, wherein the KASIII is FabH from Staphylococcus aureus S. pneumonia, Streptomyces glaucescens, A. acidocaldarius, B. vulgatus Legionella pneumophila, Aeromonas hydrophila, Bacteroides vulgatus, Brevibacterium linens, Capnocytophaga gingivalis, Thermus aquaticus, Bacillus licheniformis, Desulfovibrio vulgaris, Bacillus subtilis, S. Haliangium ochraceum, or Alicyclobacillus acidocaldarius.

9. The bacteria cell of claim 3, wherein the propionyl-CoA synthetase is from Salmonella enterica (Se prpE$^+$).

10. The bacteria cell of claim 3, wherein the glyoxylate reductase is from Arabidopsis thaliana (At GLYR$^+$).

11. The bacteria cell of claim 3, wherein the isocitrate lyase is from E. coli MG1655 (Ec IL$^+$).

12. The bacteria cell of claim 1, comprising one of the following genotypes:
a) TE$^+$ and FabH$^+$ and prpE$^+$;
b) Rc TE$^+$ and Sa FabH$^+$ and SE PrpE$^+$;
c) Rc TE$^+$ and Bs FabH$^+$ and SE PrpE$^+$;
d) Ua TE$^+$ and Sa FabH$^+$ and SE PrpE$^+$;
e) Ua TE$^+$, Bs FabH$^+$ and SE PrpE$^+$;
f) any of a-e) with add IL$^+$ and GLYR$^+$;
g) any of a-e) with add EC IL$^+$ and AT GLYR$^+$;
h) any of a-e) with add IL$^+$ and GLYR$^+$ and deleted endogenous Δicd and ΔaceB;
i) any of a-e) with add EC IL$^+$ and AT GLYR$^+$ and deleted endogenous Δicd and ΔaceB;
j) any of a-e) with add PYC$^+$ and AAT$^+$ and PAND$^+$;
k) any of a-e) with add PYC$^+$ and AAT$^+$ and PAND$^+$ and PAL$^+$; or
l) any of a-k) with add ΔfadD;
wherein Ec=E, coli, Rc=Ricimus communis, Se=Salmonella enterica, At=arabidopsis thaliana, Sa=Staphylococcus aureus, Bs=Bacillus subtilis, and Ua=Umbellularia californica.

13. The engineered bacterial cell of claim 1, further comprising overexpressed alcohol dehydrogenase (AlkJ) or aldehyde dehydrogenase (AlkH) or both AlkJ and AlkH.

14. An engineered bacteria cell comprising overexpressed enzymes including:
a) acyl-ACP thioesterase (TE);
b) β-ketoacyl-ACP synthase III (KASIII) with substrate specificity for an omega functionalized-CoA primer;
c) a CoA synthase able to convert a primer precursor to said omega functionalized-CoA primer;
d) optionally reduced expression of any endogenous KASI, KASII or KASIII having a substrate preference for acetyl-coA and propionyl-CoA; and,
e) one of the following:
i) overexpression of a propionyl-CoA synthetase, a glyoxylate reductase, an isocitrate lyase, and deactivation of endogenous malate synthase A, endogenous isocitrate dehydrogenase, and endogenous acyl-CoA synthetase,
ii) overexpression of pyruvate carboxylase (E.C. 6.4.1.1), acetate-CoA transferase (E.C. 2.8.3.8); and aspartate 1-decarboxylase (E.C. 4.1.1.11), or
iii) overexpression of pyruvate carboxylase (E.C. 6.4.1.1), acetate-CoA transferase (E.C. 2.8.3.8), aspartate 1-decarboxylase (E.C. 4.1.1.11) and beta-alanyl-CoA ammonia-lyase (EC 4.3.1.6).

15. A method of producing alpha-omega bi-functional C6-16 fatty acids, comprises the steps of:
a) culturing the engineered bacterial cell of claim 1 in a medium under conditions suitable for growth and production of alpha-omega bifunctional C6-16 fatty acids;
b) isolating said alpha-omega bifunctional C6-16 fatty acids or their derivatives from the bacterial cell or the medium or both, c) wherein said alpha-omega bifunctional C6-16 fatty acids are selected from omega-hydroxy fatty acids, alpha omega dicarboxylic fatty acids, omega aldehyde fatty acids, omega amino fatty acids, fatty acids with a double bond at the omega position, omega halogenated fatty acids, omega phenyl fatty acids, omega cyclic fatty acids and omega branched fatty acids.

\* \* \* \* \*

UNITED STATES PATENT AND TRADEMARK OFFICE
CERTIFICATE OF CORRECTION

PATENT NO. : 10,774,349 B2
APPLICATION NO. : 15/572099
DATED : September 15, 2020
INVENTOR(S) : Ka-Yiu San and Dan Wang Page 1 of 1

It is certified that error appears in the above-identified patent and that said Letters Patent is hereby corrected as shown below:

In the Claims

Column 32, Lines 20-33, (approx.) Claim 12:
In clauses f) through l), the word "add" should be "added";
In clauses g) and i), the term "AT" should be "At";
In the "wherein" clause, the microorganism "E, coli" should be "E. coli", and "At=arabidopsis thaliana" should be "At=Arabidopsis thaliana";
In clauses h) and i), the "Delta.icd and Delta.aceB" should be italized;
In clause l), the "Delta.fadD" should be italized;
In the "wherein" clause, the names of the microorganisms should also be italized ("Rc=Ricimus communis, Se=Salmonella enterica, At=Arabidopsis thaliana, Sa=Staphylococcus aureus, Bs=Bacillus subtilis, and Ua=Umbellularia califomica").

Signed and Sealed this
Twenty-fourth Day of November, 2020

Andrei Iancu
*Director of the United States Patent and Trademark Office*